US008940286B2

(12) United States Patent
Matsuo et al.

(10) Patent No.: US 8,940,286 B2
(45) Date of Patent: Jan. 27, 2015

(54) URATE TRANSPORTER, AS WELL AS METHOD AND KIT FOR EVALUATING URATE TRANSPORT-RELATED DISEASE FACTOR AND INFLAMMATION-RELATED DISEASE FACTOR, AND TEST SAMPLE AND DRUG

(75) Inventors: Hirotaka Matsuo, Saitama (JP); Nariyoshi Shinomiya, Saitama (JP); Takahiro Nakamura, Tokyo (JP); Tappei Takada, Tokyo (JP); Hiroshi Suzuki, Saitama (JP); Yuki Ikebuchi, Tokyo (JP); Kousei Ito, Tokyo (JP); Kimiyoshi Ichida, Tokyo (JP)

(73) Assignees: The University of Tokyo, Tokyo (JP); Tokyo University of Pharmacy and Life Sciences, Tokyo (JP)

( * ) Notice: Subject to any disclaimer, the term of this patent is extended or adjusted under 35 U.S.C. 154(b) by 200 days.

(21) Appl. No.: 13/379,346

(22) PCT Filed: Jun. 22, 2010

(86) PCT No.: PCT/JP2010/004154
§ 371 (c)(1),
(2), (4) Date: Jun. 19, 2012

(87) PCT Pub. No.: WO2010/150525
PCT Pub. Date: Dec. 29, 2010

(65) Prior Publication Data
US 2012/0255044 A1 Oct. 4, 2012

(30) Foreign Application Priority Data

Jun. 22, 2009 (JP) ................................. 2009-148106

(51) Int. Cl.
*A61K 48/00* (2006.01)
*A61K 38/00* (2006.01)
*C07K 14/47* (2006.01)
*C07K 14/705* (2006.01)
*G01N 33/566* (2006.01)
*G01N 33/68* (2006.01)

(52) U.S. Cl.
CPC .......... *C07K 14/705* (2013.01); *G01N 2800/34* (2013.01); *G01N 33/566* (2013.01); *G01N 2800/24* (2013.01); *G01N 2800/32* (2013.01); *G01N 33/6893* (2013.01)
USPC .......... 424/78.38; 514/283; 530/350

(58) Field of Classification Search
CPC .......... A61K 48/00; A61K 38/00; C07K 14/47
USPC .......... 424/78.38; 514/283; 530/350
See application file for complete search history.

(56) References Cited

FOREIGN PATENT DOCUMENTS

| CA | 2784286 | 12/2010 |
|---|---|---|
| JP | 2003093067 | 4/2003 |
| JP | 2007060967 | 3/2004 |
| JP | 2004016042 | 1/2006 |
| JP | 2005529618 | 3/2006 |
| JP | 2011519596 | 5/2011 |

OTHER PUBLICATIONS

Krishnamurthy et al. 2006,first published 2005; Role of ABCG2/BCRP in Biology and Medicine. Annual Review of Pharmacology and Toxicology. 46: 381-410.*
PCT/JP2010/004154 PCT counterpart of the instant application, Jun. 22, 2010, Matsuo, et al.
PCT/JP2010/004154 International search report, Jun. 22, 2010, Matsuo, et al.
PCT/JP2010/004154 International preliminary report on patentability, Jun. 22, 2010, Matsuo, et al.
Dehghan, A. et al. Association of three genetic loci with uric acid concentration and risk of gout: a genome-wide association study. Lancet 372: 1953-1961 (2008).
Enomoto, A. et al. Molecular identification of a renal urate anion exchanger that regulates blood urate levels. Nature 417: 447-452 (2002).
Hisashi, Y. et al. The Japanese journal of clinical nutrition 100(4): 393-401 (Apr. 2002). (English abstract not provided, cited in the written opinion of the international searching authority and the international search report. Refer to PCT/JP2010/004154).
Huls, M. et al. The breast cancer resistance protein transporter ABCG2 is expressed in the human kidney proximal tubule apical membrane. Kidney Int 73: 220-225 (2008).
Kolz, M. et al. Meta-analysis of 28, 141 individuals identifies common variants with five new loci that influence uric acid concentrations. Plos genetics 5(6): 1-10 (2009).

(Continued)

*Primary Examiner* — Karen Cochrane Carlson
(74) *Attorney, Agent, or Firm* — Brian S. Boyer; Syndicated Law, PC

(57) ABSTRACT

A method and evaluation kit are provided, in which a high-capacity urate transporter is identified to assist in the early treatment and prevention of urate transport-related disease and inflammation-related disease. The method can include a step for detecting variations in genes that encode ABCG2 protein. When a subject has an SNP of V12M, R113X, Q126X, Q141K, F208S, G268R, E334X, S441N, L447V, S486N, F506SfsX4, R575X, and/or C608X, it can be concluded that the subject has a factor that is capable of inducing urate transport failure, or a state or disease attributable to that failure. When a subject has an SNP of V12M, it can be concluded that, unlike the other SNPs, there is a possibility that the subject does not possess such a factor because, although this variation itself does not lead to a change in urate transport capability, said variation is related to linkage disequilibrium with other SNPs.

11 Claims, 16 Drawing Sheets

(56) References Cited

OTHER PUBLICATIONS

Kondo, C. et al. Functional analysis of SNPs variants of BCRP/ABCG2. Pharm res 21: 1895-903 (2004).

Maekawa, K. et al. Genetic variation and haplotype structure of the ABC transporter gene ABCG2 in a Japanese population. Drug metab pharmacokinet 21: 109-21 (2006).

Matsuo, H. et al. Mutations in glucose transporter 9 gene SLC2A9 cause renal hypouricemia. Am journal hum genet 83: 744-51 (2008).

Nishio, K. et al. Possible interactions of the endothelial constitutive nitric oxide synthase genotype with alcohol drinking and walking time for high serum uric acid levels among Japanese. Metabolism 54(10): 1302-8 (2005).

Takenaka, K. et al. Substrate overlap between Mrp4 and Abcg2/ affects purine analougue drug cytotoxicity and tissue distribution. Cancer res 67(14): 6965-6972 (2007).

Wang, H. et al. Membrane topology of the human breast cancer resistance protein bcrp/abcg2 determined by epitope insertion and immunoflouresence. Biochemistry 47: 13778-87 (2008).

PCT/JP2010/004154 Written opinion of the searching authority, Jun. 22, 2010, Matsuo, et al.

Woodward, O. M. et al. Identification of a urate transporter, ABCG2, with a common functional polymorphism causing gout. Proc Natl acad sci USA 106(25): 10338-10342 (2009).

\* cited by examiner

FIG. 7
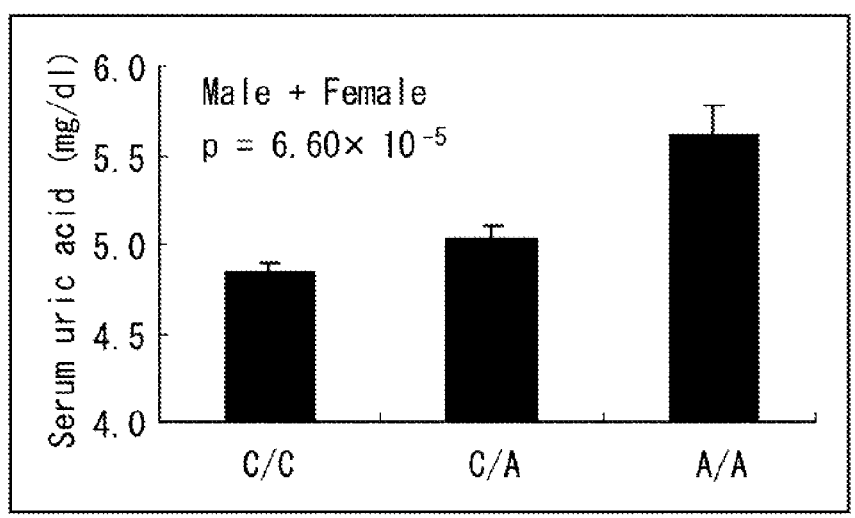
(A)
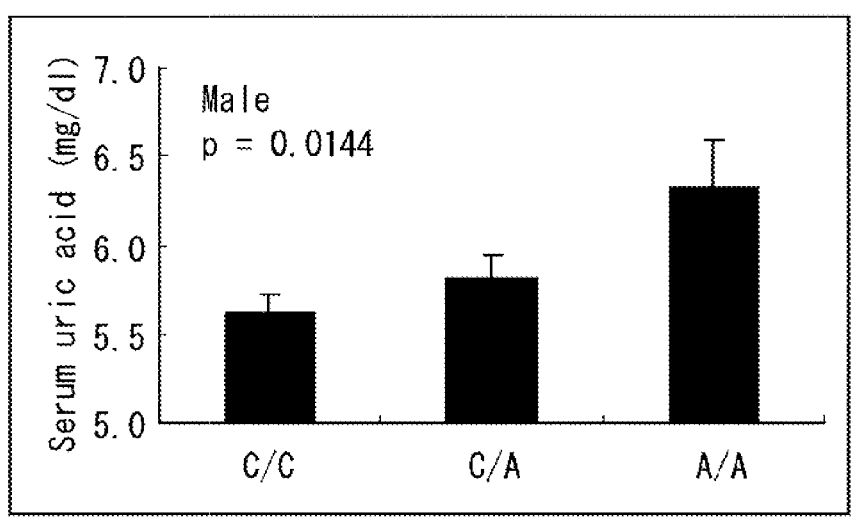
(B)
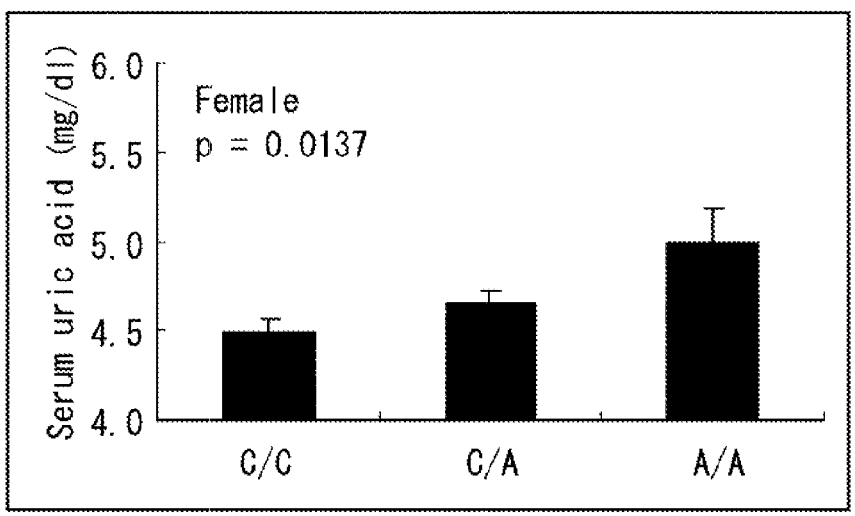
(C)

FIG. 9

| Estimated Function | Genotype | | Male | | Female | | Male + Female | |
|---|---|---|---|---|---|---|---|---|
| | Q126X | Q141K | Number | (%) | Number | (%) | Number | (%) |
| ≤1/4 function | T/T<br>T/C | C/C<br>A/C | 12 | (1.2) | 15 | (1.7) | 27 | (1.3) |
| 1/2 function | T/C<br>C/C | C/C<br>A/A | 144 | (13.8) | 134 | (12.4) | 278 | (12.9) |
| 3/4 function | C/C | A/C | 405 | (38.9) | 450 | (40.0) | 855 | (39.8) |
| full function | C/C | C/C | 481 | (46.2) | 509 | (46.0) | 990 | (46.0) |
| total | | | 1042 | (100.0) | 1108 | (100.0) | 2150 | (100.0) |

FIG. 10

| Estimated Function | Genotype Q126X | Genotype Q141K | Number Gout | Number Control | P Value | OR | 95% CI |
|---|---|---|---|---|---|---|---|
| ≤1/4 function | T/T<br>T/C | C/C<br>A/C | 37 | 22 | 3.84×10⁻¹⁴ | 10.57 | 5.87–19.03 |
| 1/2 function | T/C<br>C/C | C/C<br>A/A | 171 | 221 | <2.00×10⁻¹⁶ | 4.84 | 3.67–6.39 |
| 3/4 function | C/C | A/C | 335 | 697 | <2.00×10⁻¹⁶ | 2.73 | 2.19–3.39 |
| full funciton | C/C | C/C | 169 | 950 | | | |

FIG. 12

| genotype | | Caucasian individuals(n) | (%) | individuals of African descent(n) | (%) | Japanese individual | (%) |
|---|---|---|---|---|---|---|---|
| Q126X | C/C (wild type) | 198 | (99.50%) | 84 | (85.71%) | 2040 | (94.88%) |
| | C/T (hetero) | 1 | (0.50%) | 14 | (14.29%) | 110 | (5.12%) |
| Q141K | C/C (wild type) | 166 | (83.42%) | 86 | (87.76%) | 1073 | (49.91%) |
| | C/A (hetero) | 29 | (14.57%) | 12 | (12.24%) | 882 | (41.02%) |
| | A/A (homo) | 4 | (2.01%) | 0 | (0.00%) | 195 | (9.07%) |
| total | | 199 | (100.00%) | 98 | (100.00%) | 2150 | (100.00%) |

SEQUENCE LISTING

```
<160> NUMBER OF SEQ ID NOS: 90

<210> SEQ ID NO 1
<211> LENGTH: 9
<212> TYPE: DNA
<213> ORGANISM: Homo sapiens

<400> SEQUENCE: 1 ttaagctga                                                                 9

<210> SEQ ID NO 2
<211> LENGTH: 9
<212> TYPE: DNA
<213> ORGANISM: Homo sapiens

<400> SEQUENCE: 2 gaatatcaa                                                                 9

<210> SEQ ID NO 3
<211> LENGTH: 9
<212> TYPE: DNA
<213> ORGANISM: Homo sapiens

<400> SEQUENCE: 3 caaatcaac                                                                 9
```

```
<210> SEQ ID NO 4
<211> LENGTH: 9
<212> TYPE: DNA
<213> ORGANISM: Homo sapiens

<400> SEQUENCE: 4 gtggtacaa                                                                  9

<210> SEQ ID NO 5
<211> LENGTH: 9
<212> TYPE: DNA
<213> ORGANISM: Homo sapiens

<400> SEQUENCE: 5 gactccaag                                                                  9

<210> SEQ ID NO 6
<211> LENGTH: 9
<212> TYPE: DNA
<213> ORGANISM: Homo sapiens

<400> SEQUENCE: 6 cctgaaaag                                                                  9

<210> SEQ ID NO 7
<211> LENGTH: 9
<212> TYPE: DNA
<213> ORGANISM: Homo sapiens

<400> SEQUENCE: 7 aatcagctg                                                                  9

<210> SEQ ID NO 8
<211> LENGTH: 9
<212> TYPE: DNA
<213> ORGANISM: Homo sapiens

<400> SEQUENCE: 8 actttaaag                                                                  9

<210> SEQ ID NO 9
<211> LENGTH: 9
<212> TYPE: DNA
<213> ORGANISM: Homo sapiens

<400> SEQUENCE: 9 atagctcag                                                                  9

<210> SEQ ID NO 10
<211> LENGTH: 9
<212> TYPE: DNA
<213> ORGANISM: Homo sapiens

<400> SEQUENCE: 10 ccagaacag                                                                  9

<210> SEQ ID NO 11
<211> LENGTH: 9
<212> TYPE: DNA
<213> ORGANISM: Homo sapiens

<400> SEQUENCE: 11
```

```
gctcttcat                                                                 9
```

<210> SEQ ID NO 12
<211> LENGTH: 9
<212> TYPE: DNA
<213> ORGANISM: Homo sapiens

<400> SEQUENCE: 12

```
tcatgttag                                                                 9
```

<210> SEQ ID NO 13
<211> LENGTH: 9
<212> TYPE: DNA
<213> ORGANISM: Homo sapiens

<400> SEQUENCE: 13

```
tttatgatg                                                                 9
```

<210> SEQ ID NO 14
<211> LENGTH: 9
<212> TYPE: DNA
<213> ORGANISM: Homo sapiens

<400> SEQUENCE: 14

```
ggatttacg                                                                 9
```

<210> SEQ ID NO 15
<211> LENGTH: 9
<212> TYPE: DNA
<213> ORGANISM: Homo sapiens

<400> SEQUENCE: 15

```
ctatgcaac                                                                 9
```

<210> SEQ ID NO 16
<211> LENGTH: 9
<212> TYPE: DNA
<213> ORGANISM: Homo sapiens

<400> SEQUENCE: 16

```
tatatccta                                                                 9
```

<210> SEQ ID NO 17
<211> LENGTH: 9
<212> TYPE: DNA
<213> ORGANISM: Homo sapiens

<400> SEQUENCE: 17

```
gtgagtaaa                                                                 9
```

<210> SEQ ID NO 18
<211> LENGTH: 9
<212> TYPE: DNA
<213> ORGANISM: Homo sapiens

<400> SEQUENCE: 18

```
gtatgtaca                                                                 9
```

<210> SEQ ID NO 19
<211> LENGTH: 9
<212> TYPE: DNA
<213> ORGANISM: Homo sapiens

<400> SEQUENCE: 19

```
gtgagtata                                                              9

<210> SEQ ID NO 20
<211> LENGTH: 9
<212> TYPE: DNA
<213> ORGANISM: Homo sapiens

<400> SEQUENCE: 20 gtaagtatt                                                              9

<210> SEQ ID NO 21
<211> LENGTH: 9
<212> TYPE: DNA
<213> ORGANISM: Homo sapiens

<400> SEQUENCE: 21 gtaatgtgg                                                              9

<210> SEQ ID NO 22
<211> LENGTH: 9
<212> TYPE: DNA
<213> ORGANISM: Homo sapiens

<400> SEQUENCE: 22 gtaaatgct                                                              9

<210> SEQ ID NO 23
<211> LENGTH: 9
<212> TYPE: DNA
<213> ORGANISM: Homo sapiens

<400> SEQUENCE: 23 gtatggttg                                                              9

<210> SEQ ID NO 24
<211> LENGTH: 9
<212> TYPE: DNA
<213> ORGANISM: Homo sapiens

<400> SEQUENCE: 24 gtatatgaa                                                              9

<210> SEQ ID NO 25
<211> LENGTH: 9
<212> TYPE: DNA
<213> ORGANISM: Homo sapiens

<400> SEQUENCE: 25 gtaaccagc                                                              9

<210> SEQ ID NO 26
<211> LENGTH: 9
<212> TYPE: DNA
<213> ORGANISM: Homo sapiens

<400> SEQUENCE: 26 gtaagtaaa                                                              9

<210> SEQ ID NO 27
<211> LENGTH: 9
<212> TYPE: DNA
<213> ORGANISM: Homo sapiens
```

```
<400> SEQUENCE: 27 gtgagtagg                                                                9

<210> SEQ ID NO 28
<211> LENGTH: 9
<212> TYPE: DNA
<213> ORGANISM: Homo sapiens

<400> SEQUENCE: 28 gtaagtatg                                                                9

<210> SEQ ID NO 29
<211> LENGTH: 9
<212> TYPE: DNA
<213> ORGANISM: Homo sapiens

<400> SEQUENCE: 29 gtgagtctg                                                                9

<210> SEQ ID NO 30
<211> LENGTH: 9
<212> TYPE: DNA
<213> ORGANISM: Homo sapiens

<400> SEQUENCE: 30 gtatgtctt                                                                9

<210> SEQ ID NO 31
<211> LENGTH: 9
<212> TYPE: DNA
<213> ORGANISM: Homo sapiens

<400> SEQUENCE: 31 gtaagtttt                                                                9

<210> SEQ ID NO 32
<211> LENGTH: 9
<212> TYPE: DNA
<213> ORGANISM: Homo sapiens

<400> SEQUENCE: 32 tgtctgcag                                                                9

<210> SEQ ID NO 33
<211> LENGTH: 9
<212> TYPE: DNA
<213> ORGANISM: Homo sapiens

<400> SEQUENCE: 33 tgtttacag                                                                9

<210> SEQ ID NO 34
<211> LENGTH: 9
<212> TYPE: DNA
<213> ORGANISM: Homo sapiens

<400> SEQUENCE: 34 ctcttatag                                                                9

<210> SEQ ID NO 35
<211> LENGTH: 9
<212> TYPE: DNA
<213> ORGANISM: Homo sapiens
```

```
<400> SEQUENCE: 35 tgcccttaag                                                         9

<210> SEQ ID NO 36
<211> LENGTH: 9
<212> TYPE: DNA
<213> ORGANISM: Homo sapiens

<400> SEQUENCE: 36 gtgatttag                                                          9

<210> SEQ ID NO 37
<211> LENGTH: 9
<212> TYPE: DNA
<213> ORGANISM: Homo sapiens

<400> SEQUENCE: 37 ttaacttag                                                          9

<210> SEQ ID NO 38
<211> LENGTH: 9
<212> TYPE: DNA
<213> ORGANISM: Homo sapiens

<400> SEQUENCE: 38 ctttcatag                                                          9

<210> SEQ ID NO 39
<211> LENGTH: 9
<212> TYPE: DNA
<213> ORGANISM: Homo sapiens

<400> SEQUENCE: 39 attgcaaag                                                          9

<210> SEQ ID NO 40
<211> LENGTH: 9
<212> TYPE: DNA
<213> ORGANISM: Homo sapiens

<400> SEQUENCE: 40 tttgaaaag                                                          9

<210> SEQ ID NO 41
<211> LENGTH: 9
<212> TYPE: DNA
<213> ORGANISM: Homo sapiens

<400> SEQUENCE: 41 tcatggcag                                                          9

<210> SEQ ID NO 42
<211> LENGTH: 9
<212> TYPE: DNA
<213> ORGANISM: Homo sapiens

<400> SEQUENCE: 42 gttctatag                                                          9

<210> SEQ ID NO 43
<211> LENGTH: 9
<212> TYPE: DNA
```

```
<213> ORGANISM: Homo sapiens

<400> SEQUENCE: 43 ctgactaag                                                                 9

<210> SEQ ID NO 44
<211> LENGTH: 9
<212> TYPE: DNA
<213> ORGANISM: Homo sapiens

<400> SEQUENCE: 44 tttttgtag                                                                 9

<210> SEQ ID NO 45
<211> LENGTH: 9
<212> TYPE: DNA
<213> ORGANISM: Homo sapiens

<400> SEQUENCE: 45 gtgttatag                                                                 9

<210> SEQ ID NO 46
<211> LENGTH: 9
<212> TYPE: DNA
<213> ORGANISM: Homo sapiens

<400> SEQUENCE: 46 taatttcag                                                                 9

<210> SEQ ID NO 47
<211> LENGTH: 9
<212> TYPE: DNA
<213> ORGANISM: Homo sapiens

<400> SEQUENCE: 47 aaagataaa                                                                 9

<210> SEQ ID NO 48
<211> LENGTH: 9
<212> TYPE: DNA
<213> ORGANISM: Homo sapiens

<400> SEQUENCE: 48 tgggatcat                                                                 9

<210> SEQ ID NO 49
<211> LENGTH: 9
<212> TYPE: DNA
<213> ORGANISM: Homo sapiens

<400> SEQUENCE: 49 gttattaga                                                                 9

<210> SEQ ID NO 50
<211> LENGTH: 9
<212> TYPE: DNA
<213> ORGANISM: Homo sapiens

<400> SEQUENCE: 50 gatgatgtt                                                                 9

<210> SEQ ID NO 51
<211> LENGTH: 9
```

```
<212> TYPE: DNA
<213> ORGANISM: Homo sapiens

<400> SEQUENCE: 51 gttggaact                                                                  9

<210> SEQ ID NO 52
<211> LENGTH: 9
<212> TYPE: DNA
<213> ORGANISM: Homo sapiens

<400> SEQUENCE: 52 gatgtctaa                                                                  9

<210> SEQ ID NO 53
<211> LENGTH: 9
<212> TYPE: DNA
<213> ORGANISM: Homo sapiens

<400> SEQUENCE: 53 gttatcact                                                                  9

<210> SEQ ID NO 54
<211> LENGTH: 9
<212> TYPE: DNA
<213> ORGANISM: Homo sapiens

<400> SEQUENCE: 54 ccacagaga                                                                  9

<210> SEQ ID NO 55
<211> LENGTH: 9
<212> TYPE: DNA
<213> ORGANISM: Homo sapiens

<400> SEQUENCE: 55 atcattgtc                                                                  9

<210> SEQ ID NO 56
<211> LENGTH: 9
<212> TYPE: DNA
<213> ORGANISM: Homo sapiens

<400> SEQUENCE: 56 agcaggggt                                                                  9

<210> SEQ ID NO 57
<211> LENGTH: 9
<212> TYPE: DNA
<213> ORGANISM: Homo sapiens

<400> SEQUENCE: 57 acatgaata                                                                  9

<210> SEQ ID NO 58
<211> LENGTH: 9
<212> TYPE: DNA
<213> ORGANISM: Homo sapiens

<400> SEQUENCE: 58 gattgaagc                                                                  9

<210> SEQ ID NO 59
```

```
<211> LENGTH: 9
<212> TYPE: DNA
<213> ORGANISM: Homo sapiens

<400> SEQUENCE: 59 atttttca                                                                   9

<210> SEQ ID NO 60
<211> LENGTH: 9
<212> TYPE: DNA
<213> ORGANISM: Homo sapiens

<400> SEQUENCE: 60 gctttgcag                                                                  9

<210> SEQ ID NO 61
<211> LENGTH: 9
<212> TYPE: DNA
<213> ORGANISM: Homo sapiens

<400> SEQUENCE: 61 atgtactgg                                                                  9

<210> SEQ ID NO 62
<211> LENGTH: 655
<212> TYPE: PRT
<213> ORGANISM: Homo sapiens

<400> SEQUENCE: 62
```

Met Ser Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe

```
            225                 230                 235                 240
Ser Ile His Gln Pro Arg Tyr Ser Ile Phe Lys Leu Phe Asp Ser Leu
            245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
            275                 280                 285

Asn Pro Ala Asp Phe Phe Leu Asp Ile Ile Asn Gly Asp Ser Thr Ala
            290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Ile Thr Val Phe Lys Glu Ile Ser
            355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
                420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
    515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
            595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655
```

```
<210> SEQ ID NO 63
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 63 ttt atc cca gtg tca caa gga                                          21
Phe Ile Pro Val Ser Gln Gly
1               5

<210> SEQ ID NO 64
<211> LENGTH: 7
<212> TYPE: PRT
<213> ORGANISM: Homo sapiens

<400> SEQUENCE: 64

Phe Ile Pro Val Ser Gln Gly
1               5

<210> SEQ ID NO 65
<211> LENGTH: 21
<212> TYPE: DNA
<213> ORGANISM: Homo sapiens
<220> FEATURE:
<221> NAME/KEY: CDS
<222> LOCATION: (1)..(21)
<220> FEATURE:
<221> NAME/KEY: misc_feature
<222> LOCATION: (10)..(12)
<223> OTHER INFORMATION: The codon "rtg" codes for Val or Met

<400> SEQUENCE: 65 ttt atc cca rtg tca caa gga                                          21
Phe Ile Pro Xaa Ser Gln Gly
1               5

<210> SEQ ID NO 66
<211> LENGTH: 7
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Val or Met

<400> SEQUENCE: 66

Phe Ile Pro Xaa Ser Gln Gly
1               5

<210> SEQ ID NO 67
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 67 ttt atc cca atg tca caa gga                                          21
Phe Ile Pro Met Ser Gln Gly
1               5

<210> SEQ ID NO 68
<211> LENGTH: 7
```

```
<212> TYPE: PRT
<213> ORGANISM: Homo sapiens

<400> SEQUENCE: 68

Phe Ile Pro Met Ser Gln Gly
1               5

<210> SEQ ID NO 69
<211> LENGTH: 26
<212> TYPE: DNA
<213> ORGANISM: Homo sapiens
<220> FEATURE:
<221> NAME/KEY: CDS
<222> LOCATION: (1)..(15)

<400> SEQUENCE: 69 ggt tac gtg gta caa gtaagtatta g                              26
Gly Tyr Val Val Gln
1               5

<210> SEQ ID NO 70
<211> LENGTH: 5
<212> TYPE: PRT
<213> ORGANISM: Homo sapiens

<400> SEQUENCE: 70

Gly Tyr Val Val Gln
1               5

<210> SEQ ID NO 71
<211> LENGTH: 26
<212> TYPE: DNA
<213> ORGANISM: Homo sapiens
<220> FEATURE:
<221> NAME/KEY: CDS
<222> LOCATION: (1)..(15)
<220> FEATURE:
<221> NAME/KEY: misc_feature
<222> LOCATION: (13)..(15)
<223> OTHER INFORMATION: The codon "yaa" codes for Gln or a stop codon
      wherein the residue at this position is absent

<400> SEQUENCE: 71 ggt tac gtg gta yaa gtaagtatta g                              26
Gly Tyr Val Val Gln
1               5

<210> SEQ ID NO 72
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: May or may not be present

<400> SEQUENCE: 72

Gly Tyr Val Val Gln
1               5

<210> SEQ ID NO 73
<211> LENGTH: 26
<212> TYPE: DNA
<213> ORGANISM: Homo sapiens
<220> FEATURE:
<221> NAME/KEY: CDS
<222> LOCATION: (1)..(12)

<400> SEQUENCE: 73
```

```
ggt tac gtg gta taagtaagta ttag                              26
Gly Tyr Val Val
1
```

<210> SEQ ID NO 74
<211> LENGTH: 4
<212> TYPE: PRT
<213> ORGANISM: Homo sapiens

<400> SEQUENCE: 74

```
Gly Tyr Val Val
1
```

<210> SEQ ID NO 75
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 75

```
aga gaa aac tta cag ttc tca gca gct                          27
Arg Glu Asn Leu Gln Phe Ser Ala Ala
1               5
```

<210> SEQ ID NO 76
<211> LENGTH: 9
<212> TYPE: PRT
<213> ORGANISM: Homo sapiens

<400> SEQUENCE: 76

```
Arg Glu Asn Leu Gln Phe Ser Ala Ala
1               5
```

<210> SEQ ID NO 77
<211> LENGTH: 27
<212> TYPE: DNA
<213> ORGANISM: Homo sapiens
<220> FEATURE:
<221> NAME/KEY: CDS
<222> LOCATION: (1)..(27)
<220> FEATURE:
<221> NAME/KEY: misc_feature
<222> LOCATION: (13)..(15)
<223> OTHER INFORMATION: The codon "mag" codes for Gln or Lys

<400> SEQUENCE: 77

```
aga gaa aac tta mag ttc tca gca gct                          27
Arg Glu Asn Leu Xaa Phe Ser Ala Ala
1               5
```

<210> SEQ ID NO 78
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Gln or Lys

<400> SEQUENCE: 78

```
Arg Glu Asn Leu Xaa Phe Ser Ala Ala
1               5
```

<210> SEQ ID NO 79
<211> LENGTH: 27

```
<212> TYPE: DNA
<213> ORGANISM: Homo sapiens
<220> FEATURE:
<221> NAME/KEY: CDS
<222> LOCATION: (1)..(27)

<400> SEQUENCE: 79 aga gaa aac tta aag ttc tca gca gct                          27
Arg Glu Asn Leu Lys Phe Ser Ala Ala
1               5

<210> SEQ ID NO 80
<211> LENGTH: 9
<212> TYPE: PRT
<213> ORGANISM: Homo sapiens

<400> SEQUENCE: 80

Arg Glu Asn Leu Lys Phe Ser Ala Ala
1               5

<210> SEQ ID NO 81
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 81 cag tgt ttc agc agt gtt tca gcc gtg                          27
Gln Cys Phe Ser Ser Val Ser Ala Val
1               5

<210> SEQ ID NO 82
<211> LENGTH: 9
<212> TYPE: PRT
<213> ORGANISM: Homo sapiens

<400> SEQUENCE: 82

Gln Cys Phe Ser Ser Val Ser Ala Val
1               5

<210> SEQ ID NO 83
<211> LENGTH: 27
<212> TYPE: DNA
<213> ORGANISM: Homo sapiens
<220> FEATURE:
<221> NAME/KEY: CDS
<222> LOCATION: (1)..(27)
<220> FEATURE:
<221> NAME/KEY: misc_feature
<222> LOCATION: (13)..(15)
<223> OTHER INFORMATION: The codon "art" codes for Ser or Asn

<400> SEQUENCE: 83 cag tgt ttc agc art gtt tca gcc gtg                          27
Gln Cys Phe Ser Xaa Val Ser Ala Val
1               5

<210> SEQ ID NO 84
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Ser or Asn

<400> SEQUENCE: 84
```

Gln Cys Phe Ser Xaa Val Ser Ala Val
1               5

<210> SEQ ID NO 85
<211> LENGTH: 44
<212> TYPE: DNA
<213> ORGANISM: Homo sapiens
<220> FEATURE:
<221> NAME/KEY: CDS
<222> LOCATION: (3)..(44)

<400> SEQUENCE: 85 ga ttg aag cca aag gca gat gcc ttc ttc gtt atg atg ttt acc        44
   Leu Lys Pro Lys Ala Asp Ala Phe Phe Val Met Met Phe Thr
    1               5                  10

<210> SEQ ID NO 86
<211> LENGTH: 14
<212> TYPE: PRT
<213> ORGANISM: Homo sapiens

<400> SEQUENCE: 86

Leu Lys Pro Lys Ala Asp Ala Phe Phe Val Met Met Phe Thr
1               5                  10

<210> SEQ ID NO 87
<211> LENGTH: 44
<212> TYPE: DNA
<213> ORGANISM: Homo sapiens
<220> FEATURE:
<221> NAME/KEY: CDS
<222> LOCATION: (3)..(44)

<400> SEQUENCE: 87 ga ttg aag cca aag gca gat gcc ttc ttc gtt atg atg ttt acc        44
   Leu Lys Pro Lys Ala Asp Ala Phe Phe Val Met Met Phe Thr
    1               5                  10

<210> SEQ ID NO 88
<211> LENGTH: 14
<212> TYPE: PRT
<213> ORGANISM: Homo sapiens

<400> SEQUENCE: 88

Leu Lys Pro Lys Ala Asp Ala Phe Phe Val Met Met Phe Thr
1               5                  10

<210> SEQ ID NO 89
<211> LENGTH: 44
<212> TYPE: DNA
<213> ORGANISM: Homo sapiens
<220> FEATURE:
<221> NAME/KEY: CDS
<222> LOCATION: (3)..(32)

<400> SEQUENCE: 89 ga ttg aag cca aag gca gat gct tct tcg tta tgatgtttac cc          44
   Leu Lys Pro Lys Ala Asp Ala Ser Ser Leu
    1               5                  10

<210> SEQ ID NO 90
<211> LENGTH: 10

```
<212> TYPE: PRT
<213> ORGANISM: Homo sapiens

<400> SEQUENCE: 90

Leu Lys Pro Lys Ala Asp Ala Ser Ser Leu
1               5                   10
```

URATE TRANSPORTER, AS WELL AS METHOD AND KIT FOR EVALUATING URATE TRANSPORT-RELATED DISEASE FACTOR AND INFLAMMATION-RELATED DISEASE FACTOR, AND TEST SAMPLE AND DRUG

The instant application contains a Sequence Listing which has been submitted in ASCII format via EFS-Web and is hereby incorporated by reference in its entirety. Said ASCII copy, created on Jun. 18, 2012, is named TSUBP002.txt and is 22,058 bytes in size.

TECHNICAL FIELD

The present invention relates to a urate transporter, as well as, a method for evaluating urate transport-related disease factor and inflammation-related disease factor relating to the transporter, an evaluation kit which implements the method, and also a test sample and a drug relating to the method and kit.

BACKGROUND ART

Gout patients have recently increased and the onset age has become younger. Gout is a disease caused by tissue deposition of monosodium urate crystals, and often has the onset as a result of inflammation of the joint. Also, gout is frequently found in hyperuricemia patients, and it has long been known to have a heritable component.

Gout is often associated with hypertension, obesity, diabetes, coronary artery diseases, cerebrovascular diseases, kidney diseases and the like. Also, inflammation-related diseases include rheumatoid arthritis, infertility and the like, and early treatment and prevention of these diseases are needed.

The present inventors have demonstrated that loss-of-function mutations in two urate transporter genes, i.e., urate transporter 1 (URAT1/SLC22A12) and glucose transporter 9 (GLUT9/SLC2A9), cause renal hypouricemia using function-based genetic analysis (MIM220150 and MIM612076, respectively) (Non-Patent Literatures 1 and 2). These findings, together with their renal expression patterns, also show that URAT1 and GLUT9 mediate renal urate reabsorption in human.

However, other urate transporters have not been identified so far by such analysis, and urate transporters that increase the serum uric acid (SUA) level and have main pathogenic mutations causing gout or hyperuricemia remain unidentified.

The prior art relating to a urate transporter is disclosed in Patent Literature 1, and the prior arts relating to ABCG2 as a transporter are disclosed in Patent Literatures 2 to 4. However, the prior arts disclose the ABCG2 as a transporter of a drug, but not disclose its involvement in urate transport nor in urate transport-related disease factor and inflammation-related disease factor.

CITATION LIST

Literature

Patent Literature 1: JP-A-2003-93067, "Renal and placental urate transporters and their genes".

Patent Literature 2: JP-A-2007-60967, "Detection method of gene polymorphisms and screening method of drugs".

Patent Literature 3: JP-A-2004-16042, "Mutated polynucleotides and nucleic acid molecules which can be used for genetic diagnosis of abnormality in drug absorption involving ABCG2 protein".

Patent Literature 4: JP-A-2005-529618, "Prediction method of drug transport capability by ABCG2 polymorphism". Non-Patent Literatures Non-Patent Literature 1: Enomoto A, Kimura H, Chairoungdua A, et al., "Molecular identification of a renal urate anion exchanger that regulates blood urate levels", Nature 2002; 417:447-52.

Non-Patent Literature 2: Matsuo H, Chiba T, Nagamori S, et al., "Mutations in glucose transporter 9 gene SLC2A9 cause renal hypouricemia", Am J Hum Genet. 2008; 83:744-51.

Non-Patent Literature 3: Kondo C, Suzuki H, Itoda M, et al., "Functional analysis of SNPs variants of BCRP/ABCG2", Pharm Res 2004; 21:1895-903.

Non-Patent Literature 4: Maekawa K, Itoda M, Sai K, et al., "Genetic variation and haplotype structure of the ABC transporter gene ABCG2 in a Japanese population", Drug Metab Pharmacokinet 2006; 21:109-21.

Non-Patent Literature 5: Wang H, Lee E W, Cai X, Ni Z, Zhou L, Mao Q., "Membrane topology of the human breast cancer resistance protein (BCRP/ABCG2) determined by epitope insertion and immunofluorescence", Biochemistry 2008; 47:13778-87.

SUMMARY OF THE INVENTION

Problem to be solved by the Invention

Accordingly, the object of the present invention is to provide a method for evaluating urate transport-related disease factor and inflammation-related disease factor and to provide an evaluation kit which implements the method, and also a test sample and a drug relating to the method and kit so that a high-capacity urate transporter is identified in order to contribute to the early treatment and prevention of urate transport-related diseases and inflammation-related diseases on the basis of the identified transporter.

Solution to Problem

The urate transporter according to the present invention is characterized in that it is formed from proteins having ABCG2 and is capable of ATP-dependently exporting urate.

Preferably, the transporter does not have at least a single nucleotide polymorphism (SNP) of Q126X.

The method for evaluating urate transport-related disease factor and inflammation-related disease factor according to the present invention is a method for evaluating whether or not the subject has a factor that is capable of inducing urate transport failure, or a state or disease attributable to that failure, the method including a step of detecting variations in genes that encode an ABCG2 protein using a sample containing human genes of the subject. The urate transport-related disease factor and inflammation-related disease factor strictly mean urate transport-related disease factor and/or inflammation-related disease factor.

The detection of variations in genes that encode an ABCG2 protein may be detection of an SNP or a gene polymorphism having a relationship of linkage disequilibrium with the SNP.

For the detection of a gene polymorphism, any one of a direct sequencing method, a BAC array CGH method, a FISH method, an RFLP method, a PCR-SSCP method, an allele-specific oligonucleotide hybridization method, a TaqMan PCR method, an invader method, an HRM method, a SmartAmp method, a Q-probe method (QP method), a MALDI-TOF/MS method, a molecular beacon method, an RCA method, a UCAN method, and a nucleic acid hybridization method using a DNA chip or a DNA microarray is useful.

Subjects may be, for example, a Japanese population, a population of African descent, and a Caucasian population. The present invention can be applied similarly to the Pacific Rim population and other races.

When the subject has at least one SNP of V12M, R113X, Q126X, Q141K, F208S, G268R, E334X, S441N, L447V, S486N, F506SfsX4, R575X, and/or C608X, it can be concluded that the subject has a factor that is capable of inducing urate transport failure, or a state or disease attributable to that failure. When the subject has an SNP of V12M, it can be concluded indirectly that, unlike the other SNPs, there is a possibility that the subject does not possess a factor that is capable of inducing urate transport failure, or a state or disease attributable to that failure because, although this variation itself does not lead to a change in urate transport capability, the variation is related to linkage disequilibrium with other SNPs.

In particular, when the subject has an SNP of Q126X alone or a combination of Q126X and Q141K, it can be concluded that the subject has a factor that is capable of inducing urate transport failure, or a state or disease attributable to that failure.

Also, when the subject has a functional change of ABCG2 including a functional failure thereof without being limited to SNPs producing the above amino acid variations, it can be concluded that the subject has a factor that is capable of inducing urate transport failure, or a state or disease attributable to that failure.

Examples of such a functional change of ABCG2 including a functional failure thereof include a functional change of ABCG2 by a gene variation other than the above amino acid variations, a functional change of ABCG2 based on a change of an expression amount and the like by a gene variation in exons and introns containing a promoter and an untranslated region (UTR) of ABCG2, a functional change of ABCG2 by a change of a regulating factor such as a transcription factor, a compound and the like, a functional change of ABCG2 by CNV (copy number variant), an epigenetic change including DNA methylation, a functional change of ABCG2 by an RNA including a micro RNA and a noncoding RNA, and a functional change of ABCG2 by a change of a stabilization mechanism of the ABCG2 protein.

When a serum uric acid level is a given level or more, it can be concluded that the subject highly has a factor that is capable of inducing urate transport failure, or a state or disease attributable to that failure.

The threshold level of the serum uric acid level is preferably any level between 6.0 and 9.0 mg/dl such as, for example, 6.6, 7.0 and 8.0 mg/dl, and more preferably between 7.0 and 8.0 mg/dl.

Also, hyperuricemia may be classified into a uric acid overproduction type, an extrarenal uric acid underexcretion type, a renal uric acid underexcretion type, and a mixed type thereof, and classification of hyperuricemia may be identified on the basis of an evaluation of an ABCG2 function so as to contribute to treatment depending on its cause. In this case, findings in urine and blood may be considered concomitantly.

Examples of the urate transport-related diseases and inflammation-related diseases include hyperuricemia, gout, rheumatoid arthritis, osteoarthritis, infertility, cerebral stroke, ischemic heart disease, arrhythmia, photosensitivity, chronic kidney disease and the like.

The evaluation kit for urate transport-related disease factor and inflammation-related disease factor according to the present invention is a kit for evaluating whether or not the subject has a factor that is capable of inducing urate transport failure, or a state or disease attributable to that failure, the kit including:

means for detecting at least one SNP of V12M, R113X, Q126X, Q141K, F208S, G268R, E334X, S441N, L447V, S486N, F506SfsX4, R575X, and C608X in an ABCG2 gene, or a gene polymorphism having a relationship of linkage disequilibrium with the SNP, using a sample containing human genes of the subject.

The nonhuman animals according to the present invention are those for examining urate transport kinetics, and are characterized in that they have a deficiency of an ABCG2 gene.

The method for examining urate transport kinetics according to the present invention uses nonhuman animals having a deficiency of an ABCG2 gene, and may measure their serum uric acid levels.

Similarly, the method can be carried out using nonhuman animals overexpressing a human ABCG2 gene or a nonhuman ABCG2 gene, nonhuman animals overexpressing a human ABCG2 gene or a nonhuman ABCG2 gene containing at least one variation of V12M, R113X, Q126X, Q141K, F208S, G268R, E334X, S441N, L447V, S486N, F506SfsX4, R575X, and C608X, nonhuman cell lines or human cell lines having a deficiency of an ABCG2 gene, nonhuman cell lines or human cell lines overexpressing a human ABCG2 gene or a nonhuman ABCG2 gene, nonhuman cell lines or human cell lines overexpressing a human ABCG2 gene or a nonhuman ABCG2 gene containing at least one variation of V12M, R113X, Q126X, Q141K, F208S, G268R, E334X, S441N, L447V, S486N, F506SfsX4, R575X, and C608X, or cell membrane vesicles prepared from these cell lines.

Mice bred using a feedstuff containing oxonate which is an inhibitor of uricase which is a urate-metabolizing enzyme are useful as the nonhuman animals for examining urate transport kinetics.

The drug for urate transport-related diseases and inflammation-related diseases according to the present invention is a drug for reducing a factor that is capable of inducing urate transport failure, or a state or disease attributable to that failure, the drug containing:

a polynucleotide encoding an ABCG2 protein in the form capable of introducing it into cells.

Similarly, the drug according to the present invention is a drug for reducing a factor that is capable of inducing urate transport failure, or a state or disease attributable to that failure, the drug may include:

a polypeptide corresponding to an ABCG2 protein in the form capable of introducing it into cells.

Effects of the Invention

The present invention provides a high-capacity urate transporter, and concomitantly contributes to early treatment and prevention of urate transport-related diseases.

BRIEF DESCRIPTION OF DRAWINGS

FIG. 7 is a graph showing the results of quantitative trait locus (QTL) analysis of Q141K, and FIG. 7(A) is for male and female, FIG. 7(B) for male, and FIG. 7(C) for female.

FIG. 9 is a table showing the appearance frequency of an estimated functional decline of ABCG2 in general residents (health check examinees).

FIG. 10 is a table showing the association of a functional decline of ABCG2 in male gout patients.

FIG. 12 is a table showing the racial differences in respect of various ABCG2 variants.

DESCRIPTION OF EMBODIMENTS

Figure 1:
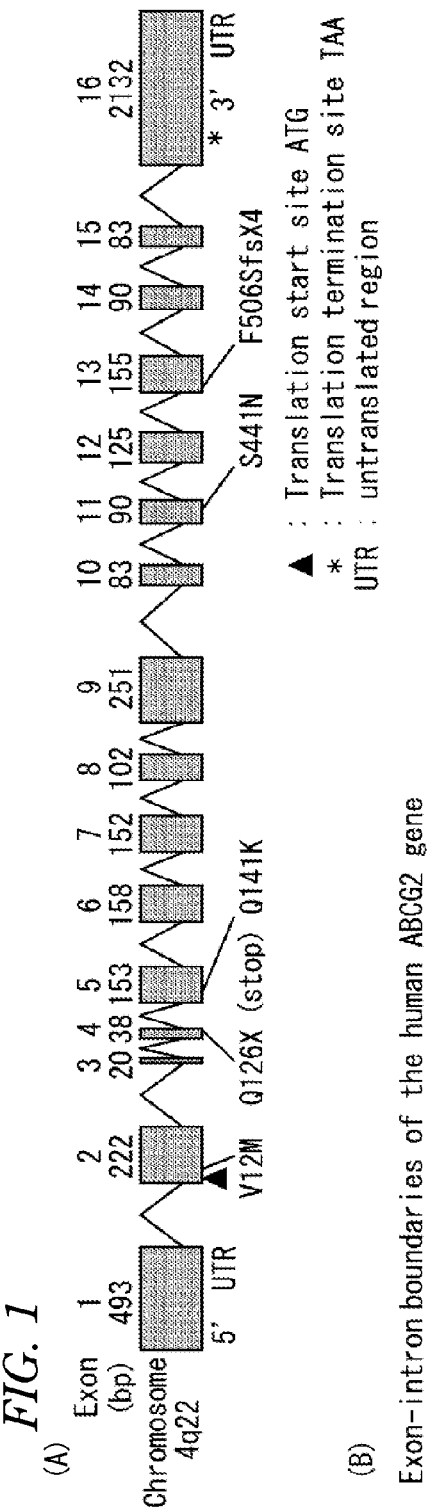
FIG. 1 is an explanatory diagram of primers (SEQ ID NOS: 1-61) for mutation analysis designed on the basis of gene structure of human ABCG2 gene.

The present inventors have found a high-capacity transporter of urate as an extension of the findings disclosed in Non-Patent Literatures 1 and 2 and the like, and thus leading to the present invention.

The present invention will be described below by showing demonstration experiments constituting the basis of the present invention. Embodiments of the present invention are not limited to the following Examples, and design can be changed by appropriately using conventionally known techniques.

Although Japanese individuals are mainly exemplified herein as the subject, the present invention can be applied similarly to other races. This is also based on the background that it is known that the prevalence of gout is high in the Pacific Rim population including Taiwanese aborigines, and the gene focused in the present invention, ABCG2, is present in a gene region on the long arm of the fourth chromosome found by a linkage study of 21 pedigrees in Taiwan with the onset of gout.

The ATP-binding cassette, subfamily G, member 2 gene ABCG2/BCRP locates in a gout-susceptibility locus (MIM138900) on chromosome 4q, and it encodes a multispecific transporter that is expressed on the apical membrane in several tissues including intestine, liver, and kidney. Also, ABCG2 is a transporter of nucleotide analogues that are structurally similar to urate (Non-Patent Literature 3).

Accordingly, as described below, the present inventors showed that ABCG2 is the first urate excretion transporter found in human and that its common variants increase serum uric acid (SUA) levels, and they performed clinicogenetic analysis of the ABCG2 gene.

In order to confirm whether or not ABCG2 exerts an adverse influence on uric acid handling and the onset of gout, a molecular-function-based clinicogenetic (FBCG) analysis was performed.

High-molecular-weight genomic DNAs were extracted from all peripheral blood cells taken from subjects. For quantitative trait locus (QTL) analysis of serum uric acid levels, genotyping of the dysfunctional common variant Q141K in 739 Japanese individuals was performed. To examine a frequency of a functional decline of ABCG2, genotyping of ABCG2 was performed in another 2150 Japanese health check examinees (1042 male individuals, 1108 female individuals).

For association studies, 228 Japanese male hyperuricemia cases (including 161 gout cases) as well as more than several hundreds of Japanese male controls (SUA≤7.0 mg/dl) were genotyped. For gout, more than 700 male cases and more than 1800 Japanese male controls (SUA≤7.0 mg/dl) were genotyped.

Female gout cases and hyperuricemia cases were also analyzed. All gout patients were clinically diagnosed as primary gout. Individuals whose serum uric acid levels had been more than 8.0 mg/dl were selected as hyperuricemia cases. To examine the presence and frequency of a functional decline of ABCG2 in individuals other than Japanese individuals, genotyping was also performed in 199 Caucasian individuals and 98 individuals of African descent.

Wild-type ABCG2 cDNA was inserted into the Nhe I site and Apa I site of pcDNA3.1(+) vector plasmid (Invitrogen, Carlsbad, Calif.), with a myc-tag sequence attached at the 5' end. To prepare membrane vesicles, HEK293 cells were transiently transfected with an expression vector for ABCG2 or an empty vector using FuGENE6 (Roche Diagnostics, Indianapolis, Ind.). Forty-eight hours later, cells were harvested and the membrane vesicles were isolated using a standard method. The uptake study of [$^3$H]estrone-3-sulfate (ES, 500 nM) and [$^{14}$C]urate (28 µM) was performed.

Using the site-directed mutagenesis technique, mutants of ABCG2 (V12M, R113X, Q126X, Q141K, F208S, G268R, E334X, S441N, L447V, S486N, F506SfsX4, R575X, C608X) were constructed on the expression vector for ABCG2, and used for urate transport analysis. Western blot analysis of the membrane vesicles (20 µg) was performed using an 800-fold diluted anti-myc-tag antibody (Roche Diagnostics).

In order to find candidate variants in ABCG2, mutation analysis of all coding regions and intron-exon boundaries of the ABCG2 gene was performed for 80 Japanese hyperuricemia patients.

FIG. 1 is an explanatory diagram of primers for mutation analysis designed on the basis of gene structure of the human ABCG2 gene.

Genomic DNA was amplified by PCR with these primers. Base sequences of the PCR products were analyzed using a 3130×1 Genetic Analyzer (Applied Biosystems, Carlsbad, Calif.). Genotyping was also performed by an allelic discrimination assay (Custom Taqman MGB, Applied Biosystems) with a 7700 detector (Applied Biosystems) or melting analysis (HRM method) with LightCycler 480 (Roche Diagnostics).

For all calculations of statistical analysis, the software R and SPSS (SPSS Japan Inc.) were used. The differences in the clinical covariates between the various genotypes of the SNPs of ABCG2 were compared using Mann-Whitney and Kruskal-Wallis tests. The Chi-square test and Fisher's exact test were used to compare the difference in genotype frequencies and allele frequencies between the gout cases and control samples. Haplotype estimation was performed using the EM algorithm. Examination of a risk of diseases such as gout due to a functional decline of ABCG2 was evaluated using logistic regression analysis.

Using membrane vesicles prepared from ABCG2-expressing cells, the inhibitory effect of urate on ABCG2-mediated transport of its typical substrate, ES (estrone-3-sulfate) was examined.

Figure 2:
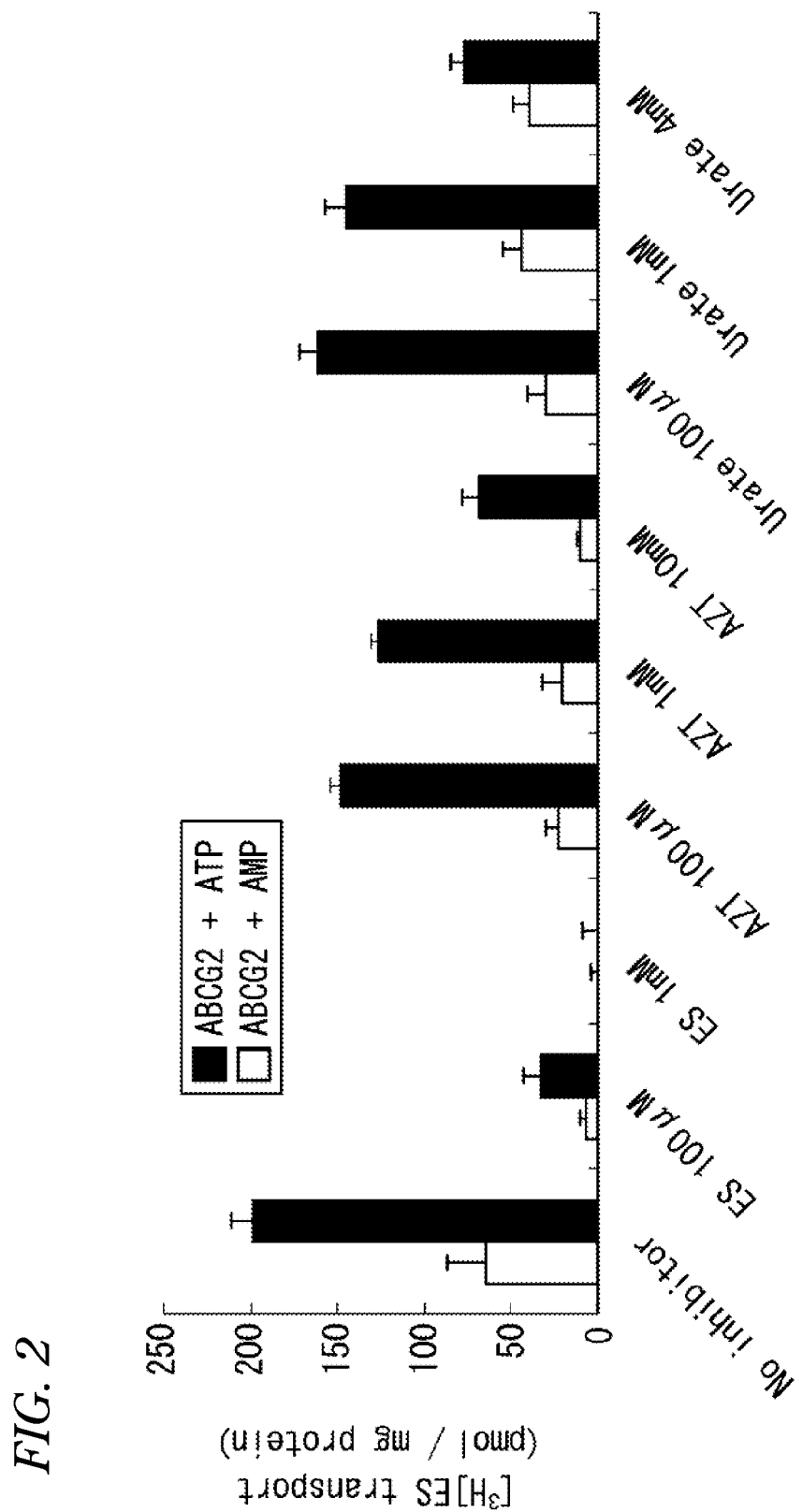
FIG. 2 is a graph showing [$^3$H] ES transport plotted against inhibitory substances.

FIG. 2 is a graph showing [$^3$H]ES transport plotted against inhibitory substances.

The inhibitory effect on the transport of [$^3$H]estrone-3-sulfate (ES, 500 nM), a typical substrate of ABCG2 was examined using the vesicle transport assay system. In addition to ES, the inhibition by another substrate, 3'-azido-3'-deoxythymidine (AZT) was observed. ES transport was also inhibited by urate, which suggests the possibility of urate transport via ABCG2.

In order to demonstrate whether or not urate is a substrate of ABCG2, transport assays were performed using isotope-labeled [$^{14}$C]urate.

Figure 3:
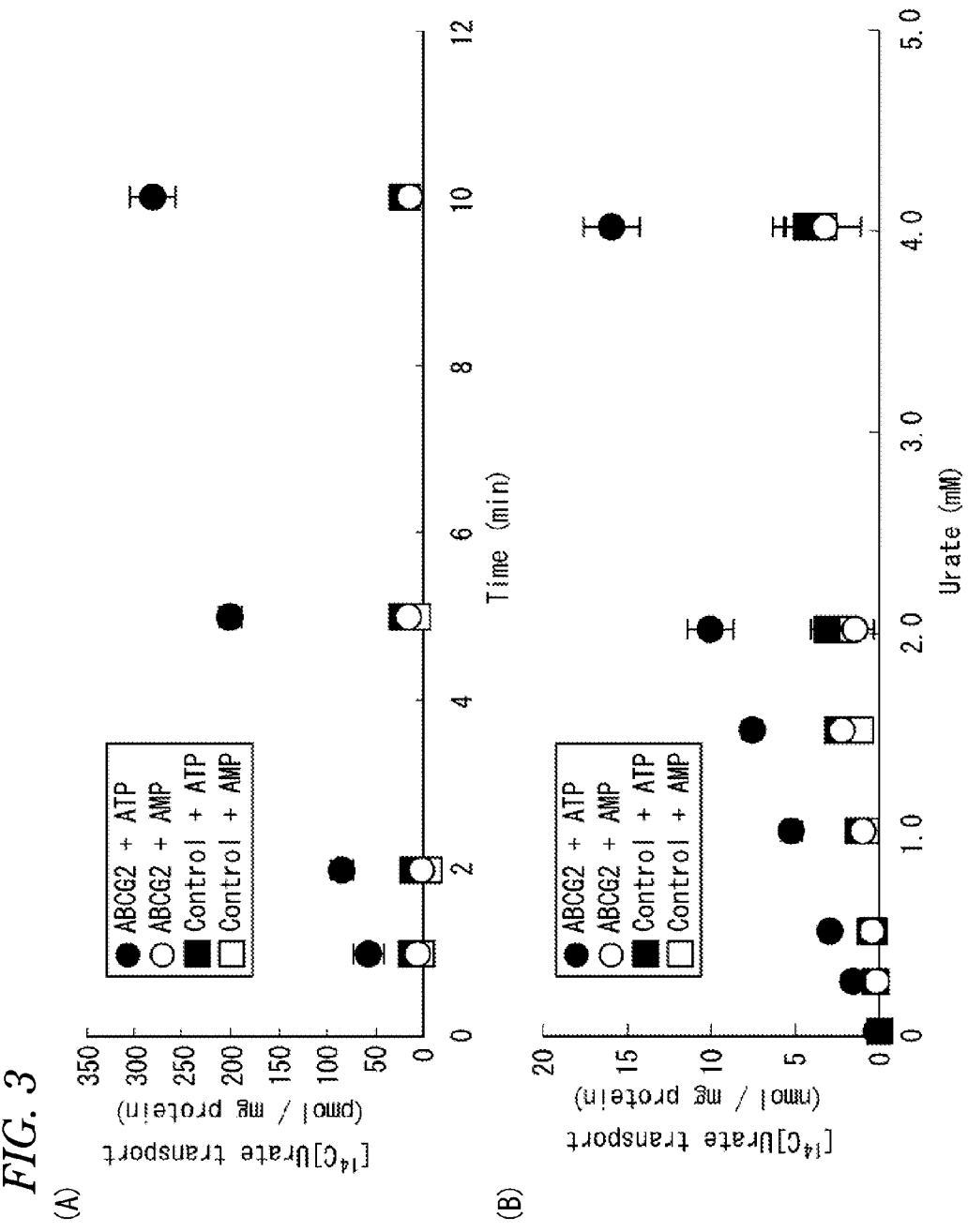
FIG. 3(a) is a graph showing [$^{14}$C] urate transport against time.
FIG. 3(b) is a graph showing [$^{14}$C] urate transport plotted against urate concentration.

FIG. 3 (A) is a graph showing [$^{14}$C]urate transport against time, and FIG. 3 (B) is a graph showing [$^{14}$C]urate transport plotted against urate concentration.

As shown in FIG. 3 (A), an ATP-dependent urate transport was detected in ABCG2-expressing vesicles but not in control vesicles. This is the first evidence of a direct high-capacity urate transport via ABCG2. Because of a mild inhibitory effect on the ES transport, urate was assumed to be a high-capacity substrate of ABCG2. Indeed, as shown in FIG. 3 (B), ABCG2-mediated urate transport scarcely reached saturation at concentrations of 1 mM or less.

Typical ABCG2 substrates, e.g., sulfate conjugates such as ES, 4-methylumbelliferone sulfate, and E3040 sulfate, are transported by ABCG2 with low capacity ($K_m$ value of about 20 µM). Kinetic analysis revealed that ABCG2 mediated the saturable transport of urate with a $K_m$ of 8.24±1.44 mM and a $V_{max}$ of 6.96±0.89 nmol/min/mg (protein), and therefore, it can be said that an ABCG2-mediated high-capacity transport remains functional under a high-urate condition.

These findings reasonably explain a newly identified physiological role of ABCG2 as a high-capacity urate exporter.

Figure 4:
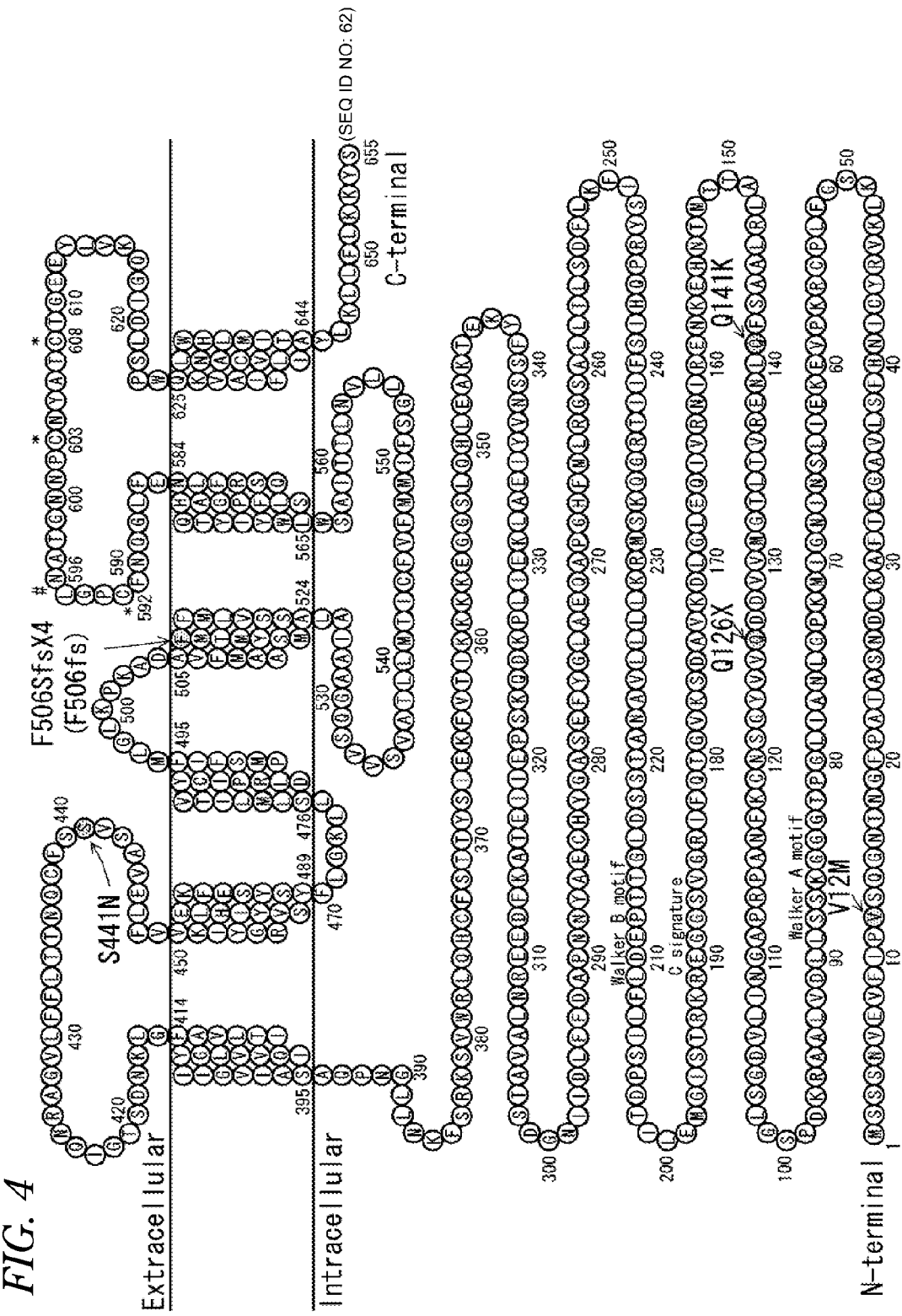
FIG. 4 shows a topology model of human ABCG2 (SEQ ID NO: 62) and the non-synonymous mutation sites found in hyperuricemia patients.
Figure 5:
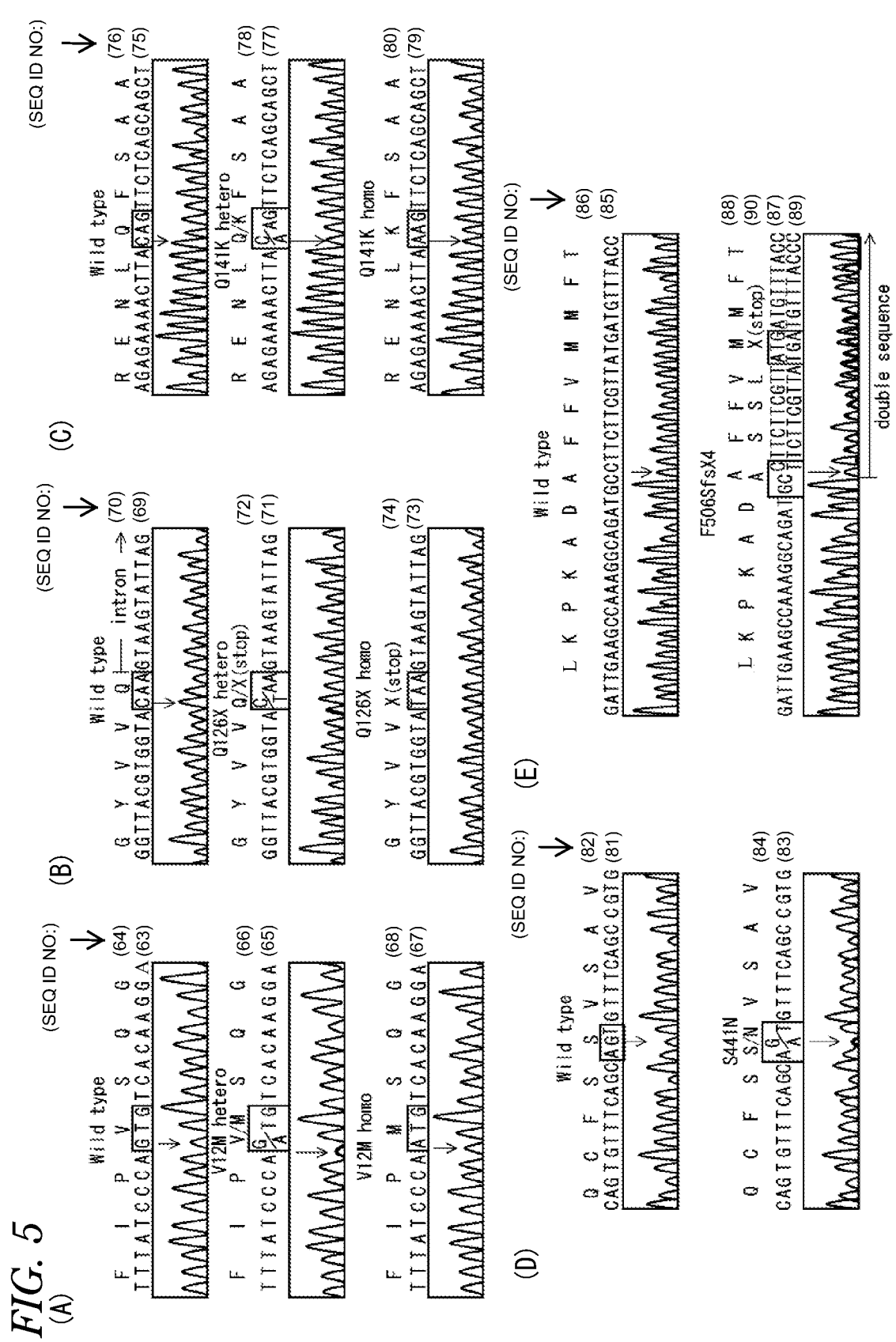
FIG. 5 shows the results of sequence analysis of ABCG2. (SEQ ID NOS: 63-90)

FIG. 4 shows a topology model of human ABCG2 and the nonsynonymous mutation sites found in hyperuricemia patients, and FIG. 5 shows the results of sequence analysis of ABCG2.

Base sequences of all coding regions of the ABCG2 gene were analyzed in 80 hyperuricemia patients, and five mutations with amino acid alterations (V12M, Q126X, Q141K, S441N, F506SfsX4) were found. "#" represents an N-linked glycosylation site (N596), and "*" represents cysteine residues for disulfide bonds (C592, C603 and C608).

V12M, Q126X and Q141K are SNPs present in the intracellular N-terminal region. It is reported that allele frequencies for these SNPs, which are quite common in the Japanese population, were 31.9% for Q141K, 19.2% for V12M, and 2.8% for Q126X (Non-Patent Literature 4). Calculations of these data on the basis of Hardy-Weinberg's equilibrium revealed that estimates of the frequencies of Japanese individuals with these minor alleles were 53.6% for Q141K, 34.7% for V12M, and 5.5% for Q126X. The topology model as shown in the figure is based on the recent report for membrane topology determination of human ABCG2 (Non-Patent Literature 5).

Figure 6:
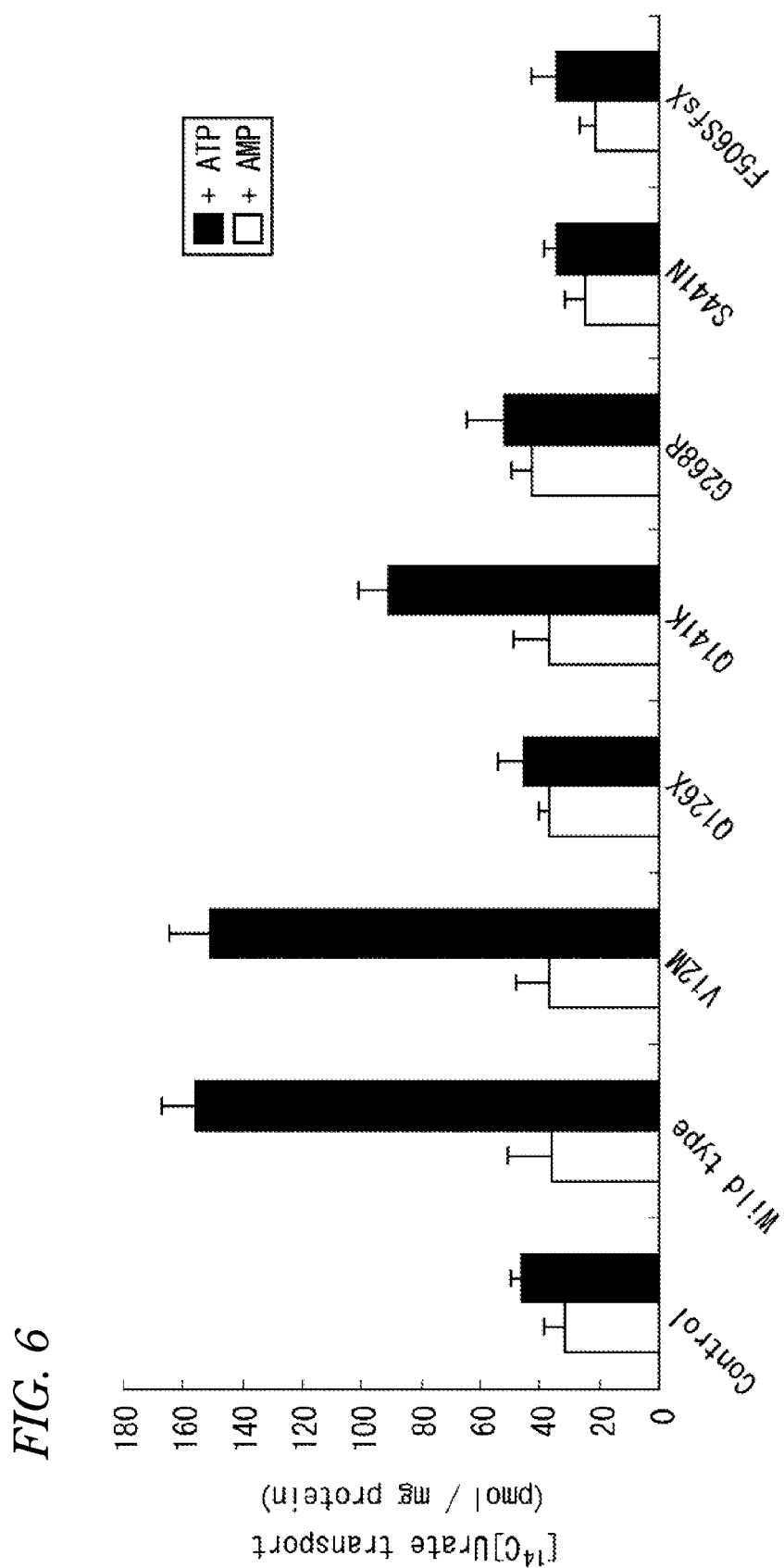
FIG. 6 is a graph showing the results of urate transport analysis of mutated ABCG2.

FIG. 6 is a graph showing the results of urate transport analysis of mutated ABCG2.

In order to clarify the effect of urate transport activities on ABCG2 function, the activities of mutants were examined using membrane vesicles expressing wild-type and mutant ABCG2 proteins.

ATP-dependent urate transport was reduced by approximately half (46.7%) in Q141K and was nearly eliminated in Q126X, G268R, S441N, and F506SfsX4 mutants. Western blot analysis showed that ABCG2 protein expression in the Q141K variant decreased by half (45.2%), while Q126X showed no protein expression on membrane vesicles. Also, ATP-dependent urate transport of ABCG2 was remarkably reduced by F208S, E334X, L447V, S486N, R575X, and C608X mutations, and was nearly eliminated in F208S, E334X, L447V, S486N, and R575X mutants.

The half-decreased urate transport activity of Q141K may be ascribed to the half-decreased expression of ABCG2 protein, which is consistent with the disclosure of Non-Patent Literature 3 on ES transport.

While loss of urate transport in the Q126X mutant should be caused by the complete lack of protein expression, V12M did not show any changes in urate transport and in protein expression relative to wild-type ABCG2. These data clearly show that the degree of decreased ABCG2 protein expression directly affects the urate transport activity.

FIG. 7 is a graph showing the results of quantitative trait locus (QTL) analysis of Q141K, and FIG. 7(A) is for male and female, FIG. 7(B) for male, and FIG. 7(C) for female.

Quantitative trait locus (QTL) analysis of serum uric acid levels was performed with the high-frequency dysfunctional variant Q141K in ABCG2, for 739 Japanese individuals including 245 male subjects and 494 female subjects. "C/C", "C/A", and "A/A" indicate wild-type subjects, heterozygous mutation carriers, and homozygous mutation carriers of Q141K, respectively.

Serum uric acid levels significantly increased as the minor alleles of Q141K increased (p=6.00×10$^{-5}$, FIG. 7 (A)). A significant increase in the serum uric acid levels was observed in both male (p=0.0144) and female (p=0.0137) subjects. Also, Q141K had no significant association with other clinical parameters such as age, body mass index, or sex.

These findings indicate that ABCG2 has a physiological function to decrease the serum uric acid levels, and that there could be great inter-individual differences in its function resulting from SNPs of ABCG2.

Figure 8:
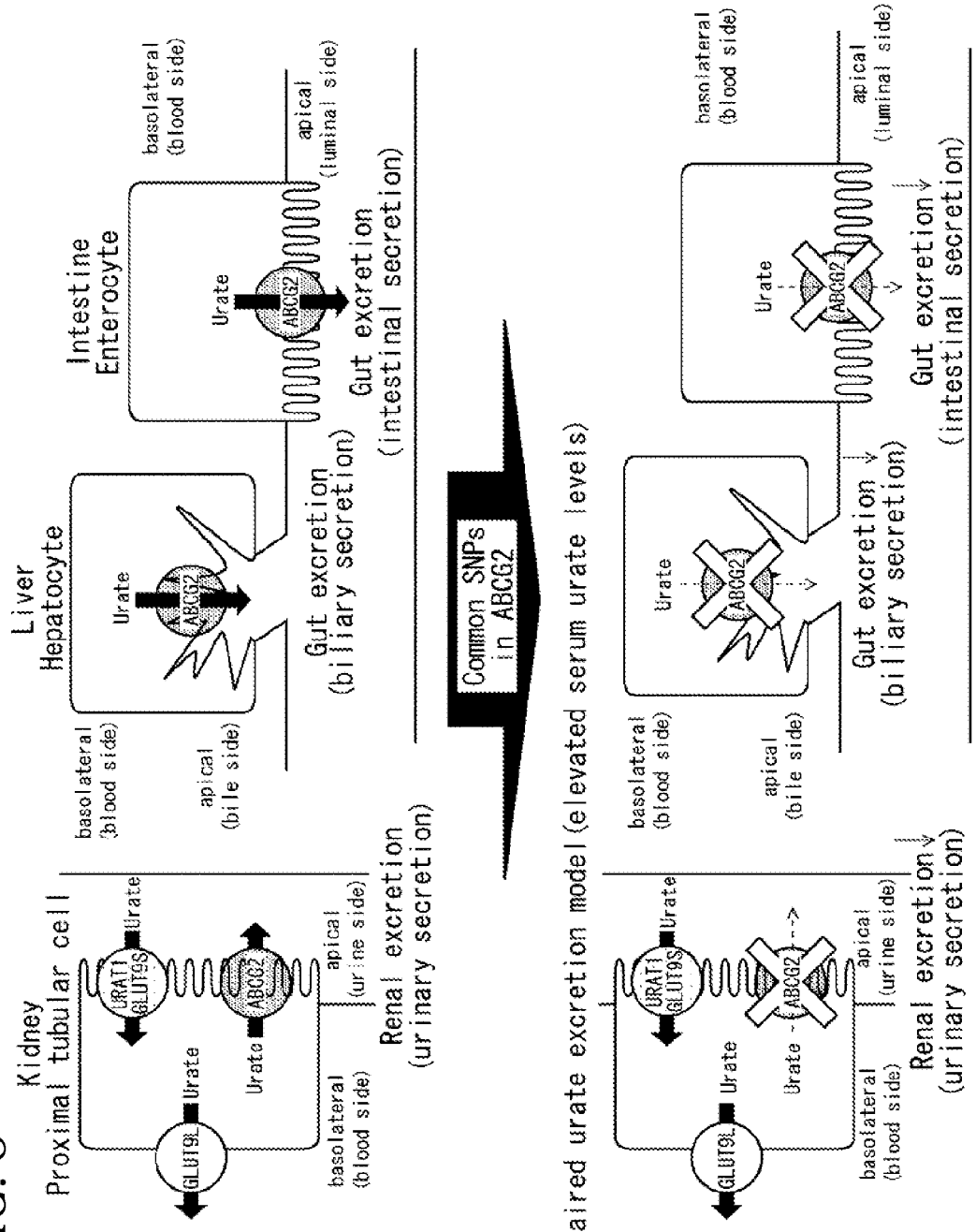
FIG. 8 shows a urate excretion model in kidney, liver and intestine.

FIG. 8 is an explanatory diagram showing a urate excretion model in kidney, liver and intestine.

Two-thirds of uric acid in the body is normally excreted through the kidney, while one-third gains entrance to the gut where it undergoes uricolysis. In the human kidney, urate is bi-directionally reabsorbed and secreted via urate transporters.

ABCG2 is expressed on the apical side of proximal tubular cells (kidney) and of hepatocytes (liver), and enterocytes (intestine). In an impaired model, common SNPs in ABCG2 on the apical side reduce the urate excretion and elevate the serum uric acid levels. Based on this impaired model, a physiological urate excretion model is proposed in which ABCG2 mediates renal urate excretion via urinary secretion.

In this model, it is also considered that ABCG2 mediates gut urate excretion via biliary and intestinal secretion. In proximal tubular cells, other urate transporters (URAT1 and GLUT9) mediate renal urate reabsorption. The location of GLUT9L (GLUT9 isoform 1) and GLUT9S (GLUT9 isoform 2) is based on observations from polarized MDCK (Madin-Darby canine kidney) cells.

Genotyping of ABCG2 SNPs for 228 Japanese male hyperuricemia cases (including 161 gout cases) was performed. If minor alleles are allele 1 and major alleles are allele 2, allele 1 is T and allele 2 is C in Q126X, allele 1 is A and allele 2 is C in Q141K, and allele 1 is A and allele 2 is G in V12M. It was found that Q126X significantly increased gout risk. Also, the dysfunctional SNP, Q141K significantly increased gout risk. Either of these mutations was observed in 80% or more gout cases. A similar observation was also recognized in an association analysis of hyperuricemia cases. Also, gout patients with Q126X homozygous mutations were observed, and furthermore, cases with Q126X homozygous mutations were also observed in asymptomatic hyperuricemia without gout. The serum uric acid level was 10 mg/dl or more in both cases.

In addition, haplotype frequency analysis of V12M, Q126X, and Q141K revealed that there is no simultaneous presence of the minor genes Q126X and Q141K in one haplotype.

The haplotype with Q126X markedly increases gout risk as compared with non-risk haplotypes. Q141K is assigned to another independent risk haplotype.

Thus, Q126X and Q141K are independent risk factors, and, merely by examining an SNP of each Q126X or Q141K, it is possible to evaluate easily whether or not a haplotype with its presence is a risk haplotype.

Also, it was found that, when the subject has a minor gene V12M (an SNP of V12M), it can be concluded indirectly that, unlike the other SNPs, there is a possibility that the subject does not possess a factor that is capable of inducing urate transport failure, or a state or disease attributable to that failure because, although this variation itself does not lead to a change in urate transport capability, the variation is related to linkage disequilibrium with other SNPs.

FIG. 9 is a table showing the appearance frequency of an estimated functional decline of ABCG2 in general residents (health check examinees). The functional decline of ABCG2 was recognized in more than half of examinees, but one-fourth or less functional decline was recognized only by about 1.2 to 1.7%. The estimated functional decline of ABCG2 was recognized similarly in male and female individuals.

FIG. 10 is a table showing the association of a functional decline of ABCG2 in male gout patients. It is clear that the onset risk becomes higher as the ABCG2 function declines. As shown in FIG. 10, the functional decline of ABCG2 was recognized in about 80% of gout cases, and 2.7-fold or more elevation of gout risk was recognized. In about 30% of gout cases, one-half or less decline of ABCG2 function was recognized, and 4.8-fold or more elevation of gout risk was recognized. Furthermore, one-fourth or less decline of function was recognized in 5% or more gout cases, and 10-fold or more increase of risk was recognized. It was found that significant increase of gout onset risk is recognized even in mild functional decline, and that the onset risk markedly increases as the functional decline is greater. Also in analysis of female gout cases, the functional decline of ABCG2 was recognized in many cases, which suggested that the decline is involved in the onset of gout.

Figure 11:
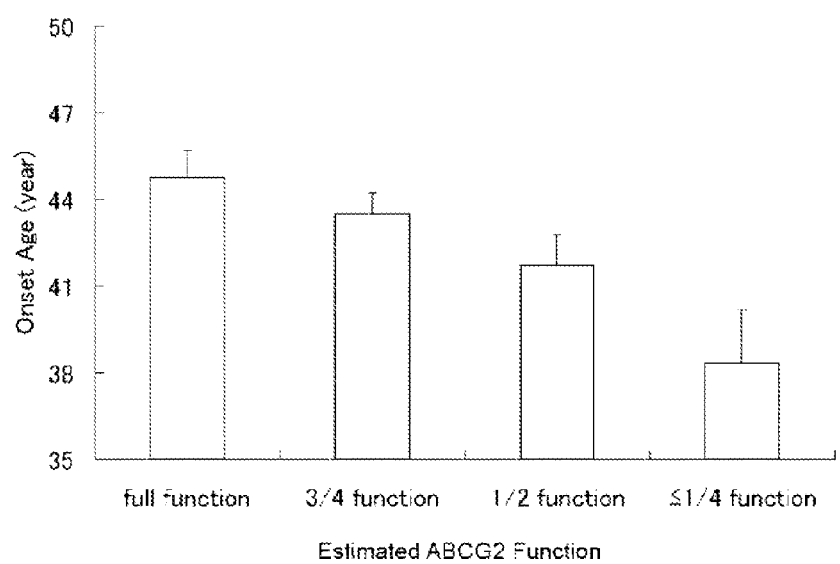
FIG. 11 is a graph showing a relationship between the ABCG2 function and the onset age.

FIG. 11 is a graph showing a relationship between the ABCG2 function and the onset age.

Analysis of more than 700 gout cases revealed that the onset age of gout becomes younger as the ABCG2 function declines. It was found that, when the ABCG2 function is ¼ below, the onset risk at the young age of twenties and younger becomes 20-fold greater than a normal risk. It was also found that, even when the ABCG2 function is ½ and ¾, the gout onset risk at the young age of twenties and younger is very high.

The functional decline of ABCG2 is closely related to the onset of gout at the young age, and therefore, early recognition of the gout risk is helpful for early prevention of the onset of gout, as well as for early treatment and prevention of worsening of symptoms when the gout is developed. Accordingly, analysis of ABCG2 function-declining SNPs and prediction of ABCG2 function based on the analysis are important to predict onset risk of diseases such as gout.

FIG. 12 is a table showing the racial differences in respect of various ABCG2 variants.

Risky variation Q126X is recognized in many individuals of African descent, and also recognized in Caucasians. Conversely, Q141K is recognized in less individuals of African descent, and in more Caucasians. Also, homo variation is recognized in Caucasian individuals, but not in individuals of African descent. Accordingly, it was found that analysis of combination of two variations is very important in individuals of African descent, and also worthy in Caucasians. In this connection, there is a possibility that analysis focused on gout cases increases the frequency.

Also, it was found that estimated ABCG2 function of ¼ or below was recognized in many individuals of African descent rich in Q126X variation to the same degree as in Japanese individuals. In individuals of African descent, the function of ¾ was less likely to be recognized (about 10%) because they are poor in Q141K as compared with other races. In Caucasians, the function of ¼ or below was less likely to be recognized because they are poor in Q126X variation, but the function of ¾ was recognized more frequently (about 15%) as compared with individuals of African descent because they are rich in Q141K.

As is apparent from these results, analysis of ABCG2 function-declining SNPs and prediction of ABCG2 function based on the analysis are important to predict onset risk of diseases such as gout, not only in Japanese individuals but also in individuals of African descent and Caucasians.

In order to clarify the role of ABCG2 in urate kinetics, analysis was performed using an animal model. The present inventors examined using mice whether or not mouse Abcg2 has a urate transport capability in the same manner as in human ABCG2, by a transport experiment using cell membrane vesicles.

Since most mammals other than some primates including human have urate-metabolizing enzyme, uricase, use of untreated mice is improper for a model reflecting human urate kinetics. Accordingly, mice to which a uricase inhibitor, potassium oxonate was daily administered were used. The administration was performed by breeding mice using an oxonate-containing feedstuff which was prepared by adding 2.0% (w/w) potassium oxonate (TokyoChemical Industry, Tokyo, Japan) to MF feed stuff (Oriental Yeast Co., Ltd., Tokyo, Japan).

A mouse Abcg2 expression vector was constructed by amplifying a cDNA of mouse Abcg2 with a myc tag sequence attached to the N-terminus, integrating it into pGEM T-Easy Vector (Promega, Madison, Wis.), and then integrating it into a Not I site of a pcDNA3.1(+) vector via a restriction enzyme treatment.

In order to confirm the expression of mouse Abcg2 via the myc-mAbcg2/pcDNA3.1(+) vector thus prepared, the vector was transiently introduced into polarized cells, LLC-PK1 cells, and the localization pattern was observed. The cells were immunostained using an anti-myc antibody and observed by a confocal microscope. The results showed that the mouse Abcg2 is localized on the apical membrane surface of the LLC-PK1 cells, and the results were consistent with the localization in a living body.

Also, in order to confirm whether or not the mouse Abcg2 transports urate in the same manner as in human ABCG2, HEK293 cells into which the mouse myc-Abcg2 expression vector was transiently introduced were recovered, and cell membrane vesicles were prepared. In order to confirm the expression of mouse myc-Abcg2, western blotting was performed, and a band was observed at the location of about 85 kDa.

Small gut excised from wild-type FVB mice and Abcg2-deficient mice (body weight 27-32 g) bred using an oxonate-containing feedstuff was divided into 3 portions, and a transport experiment was performed using the most upstream portion. One end of the gut tract was connected to a 5 ml syringe and the other end to a 2.5 ml syringe. As a mucosal side solution, 5 ml of Ringer Buffer previously warmed to 37° C. was introduced through the 5 ml syringe to fill lumen of the gut tract. Ringer Buffer at pH 7.4 containing 0.02 µCi/ml radioisotope-labeled uric acid (final concentration of radioisotope uric acid 400 nM) was warmed at 37° C. for 30 minutes with aeration of an oxygen-carbon dioxide mixed gas, and the experiment was then started by setting the time point when the gut tract was set to 0 minute.

Figure 13:
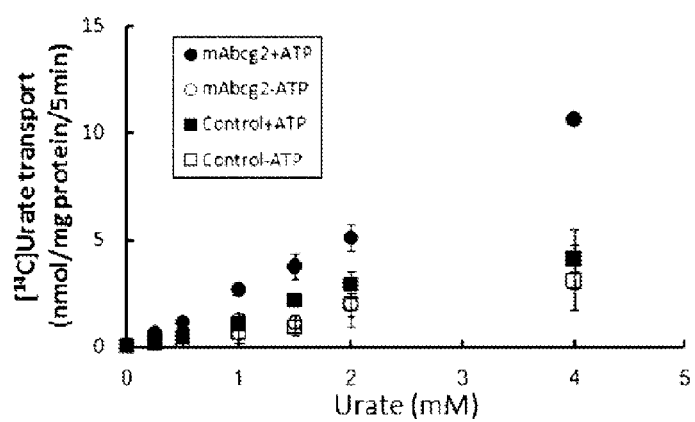
FIG. 13 is a graph showing the transport of [$^{14}$C] urate via mouse Abcg2.

FIG. 13 is a graph showing the transport of [$^{14}$C]urate via mouse Abcg2.

Transport experiments were performed using cell membrane vesicles and using radioisotope-labeled uric acid as a substrate. As a result, it was confirmed that the mouse Abcg2 also transports uric acid in the same manner as in human ABCG2. Also, transport experiments were performed in uric acid concentrations of 250 µM, 500 µM, 1 mM, 1.5 mM, 2 mM, and 4 mM, respectively. As a result, no saturability was found in this concentration range. Whereby, it was shown that mouse Abcg2 is a high-capacity urate transporter which can function even in the presence of a high concentration of uric acid.

Figure 14:
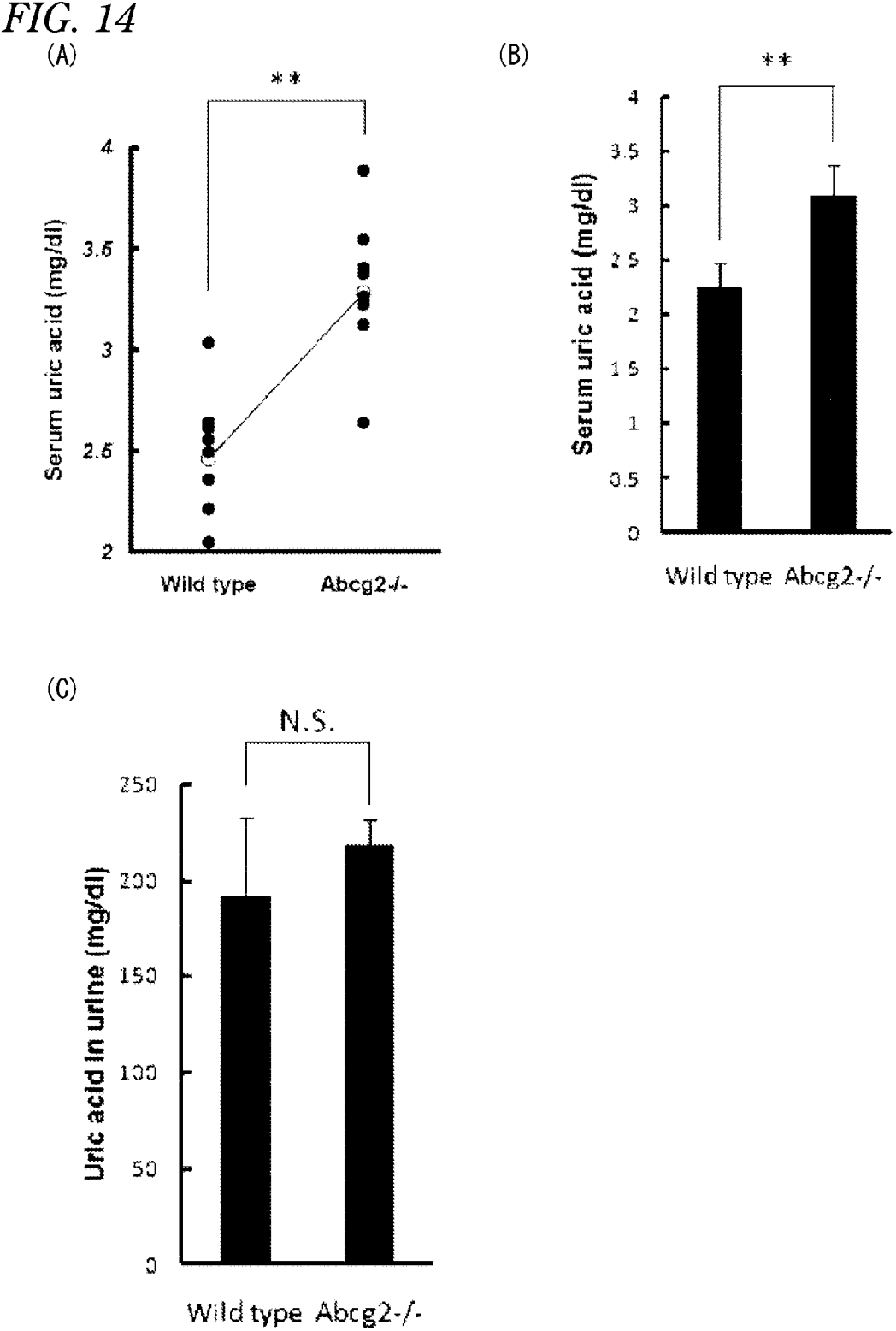
FIG. 14 is a graph showing blood uric acid levels and urinary uric acid levels in wild-type mice and ABCG2-deficient mice.

FIG. 14 is a graph showing blood uric acid levels and urinary uric acid levels in wild-type mice and Abcg2-deficient mice.

Blood uric acid levels were compared between wild-type mice and Abcg2-deficient mice receiving an oxonate-containing feedstuff for 2 or more weeks. As a result, it was found that blood uric acid levels in Abcg2-deficient mice significantly increased as compared with those in wild-type mice (FIG. 14 (A)). Since the elevation of blood uric acid levels due to the decline of Abcg2 function was confirmed in mice in the same manner as in human, the mouse model can be used as a model reflecting urate kinetics in human. Also, with a significant elevation of blood uric acid levels (FIG. 14 (B)), urinary uric acid levels also showed an elevation tendency although it was not significant (FIG. 14 (C)). The ratio of urinary uric acid levels/blood uric acid levels, corrected using urine concentrations and blood concentrations of creatinine which serves as an indicator of a renal function, significantly increased in Abcg2-deficient mice. The results show that the cause of an elevation of blood uric acid levels due to an Abcg2 deficiency can not be explained by a decrease of urinary uric acid excretion amount.

Urate transport experiments were performed using the small intestine isolated from wild-type mice and Abcg2-deficient mice.

Since uric acid secretion from the gut tract is known as a uric acid excretion pathway other than urinary excretion, the small intestine was isolated from wild-type mice and Abcg2-deficient mice, and transport experiments of radioisotope-labeled uric acid were performed. As a result, a linear urate transport was recognized up to 30 minutes both in wild-type mice and in Abcg2-deficient mice, and the transport amount of uric acid at 30 minutes significantly decreased in Abcg2-deficient mice. Whereby, it was suggested that mouse Abcg2 is involved in the urate transport in the small intestine.

Figure 15:
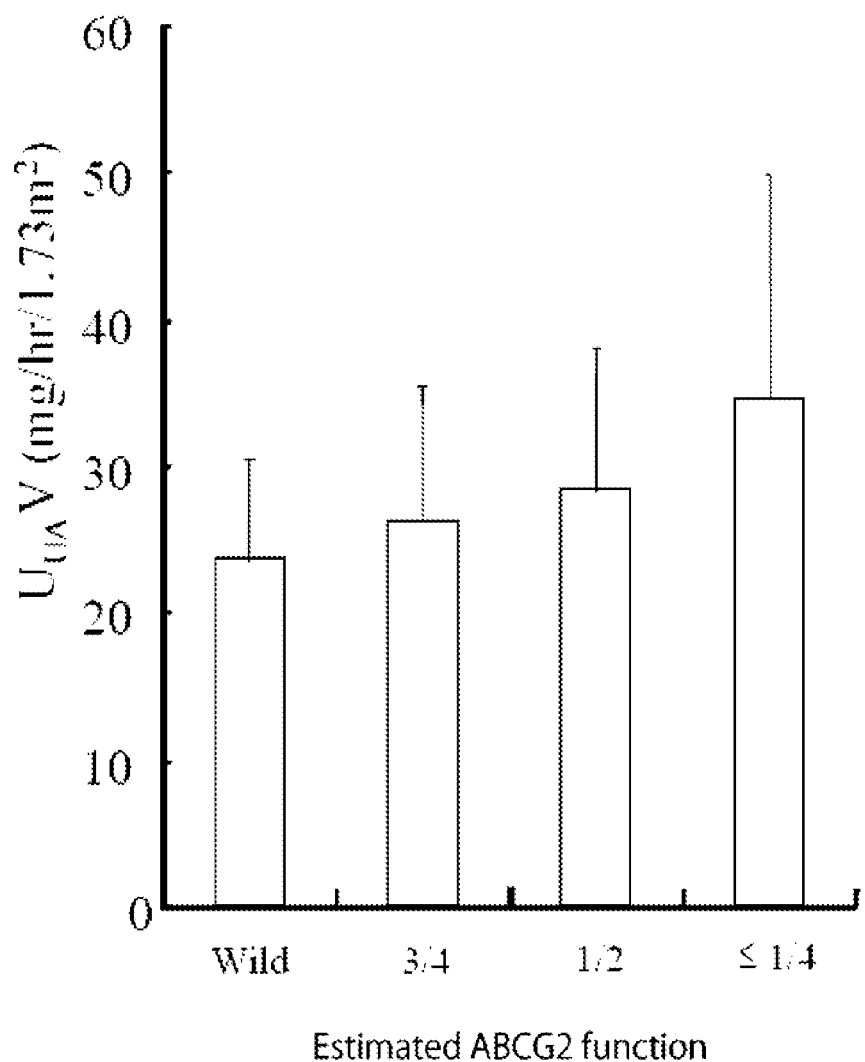
FIG. 15 is a graph showing a relationship between the ABCG2 function and the urinary uric acid excretion amount in gout and hyperuricemia patients.

FIG. 15 is a graph showing a relationship between the ABCG2 function and the urinary uric acid excretion amount (UUAV) in gout and hyperuricemia patients (cases diagnosed by physicians).

It is understood that the urinary uric acid excretion amount tends to increase as the ABCG2 function declines. The increase of the urinary uric acid excretion amount is a characteristic feature of hyperuricemia referred to as a uric acid overproduction type.

Figure 16:
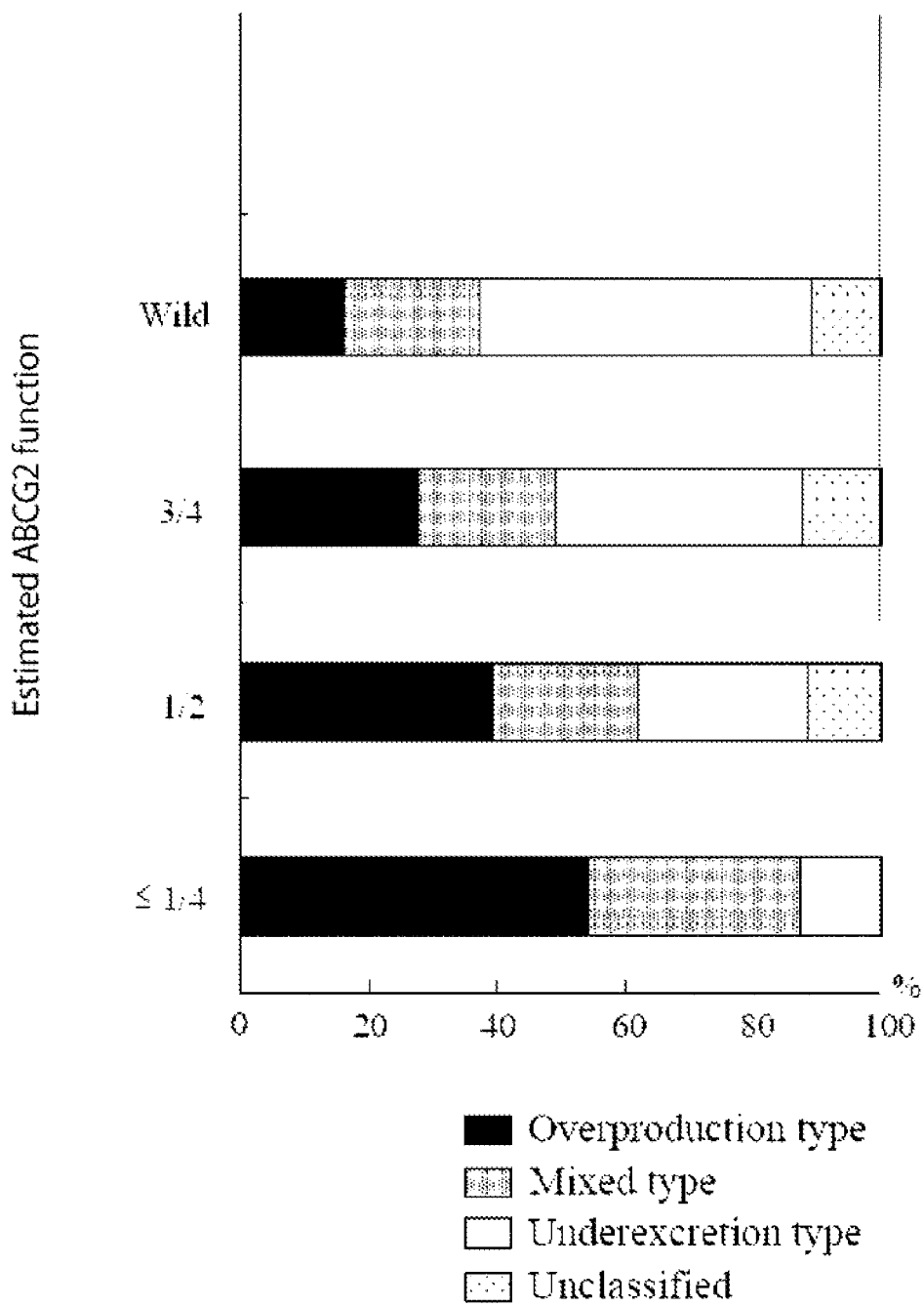
FIG. 16 is a graph showing the percentage of a traditional type of clinical classifications in hyperuricemia cases having each estimated ABCG2 function.

FIG. 16 is a graph showing the percentage of a traditional type of clinical classifications in hyperuricemia cases having each estimated ABCG2 function.

It can be said that the percentage containing a uric acid overproduction type and a mixed type is high as the ABCG2 function declines. Also, it can be recognized that patients having decline of the ABCG2 function are frequently recognized in the uric acid overproduction type and mixed type (80% or more), and conversely, patients having decline of the ABCG2 function are poorly recognized in a urinary uric acid underexcretion type.

It was found that, in the traditional overproduction type, any functional decline of ABCG2 is recognized in about 80 to 90% of the cases. It was also found that, even in the mixed type, any functional decline of ABCG2 is recognized in about 70 to 80% of the cases.

Evaluation of the ABCG2 function enabled a new, more precise clinical classification of hyperuricemia.

Thus, it was found that, in fact, many cases handled as the uric acid overproduction type in a traditional classification are not caused by the overproduction, but their pathogenesis lies in an extrarenal uric acid underexcretion caused by a functional decline of ABCG2. It was found that the cases are a uric acid overexcretion type in the kidney (renal overexcretion type) just like the traditional uric acid overproduction type.

It was found that, in the traditional overproduction type, any functional decline of ABCG2 is frequently recognized, and therefore, a type caused by decrease of extrarenal excretion of uric acid (extrarenal uric acid underexcretion type) constitutes a majority.

Previously, it was considered that excretion into urine is important as a uric acid excretion pathway, and elevation of a blood uric acid level is mainly caused by decrease of a uric acid amount excreted into urine and a uric acid overproduction. Also in clinical practice, the elevation of a blood uric acid level was considered by classifying into the urinary uric acid underexcretion type and uric acid overproduction type. Mainstream prediction and discussion were that ABCG2 assumes a function of a uric acid excretion in the kidney, and a urinary uric acid excretion clearance decreases by a deficiency of ABCG2.

To the contrary, the present inventors showed that, in Abcg2-deficient mice receiving an oxonate-containing feedstuff, the ratio of urinary uric acid levels/blood uric acid levels significantly increased, when corrected using urine concentrations and blood concentrations of creatinine which serves as an indicator of a renal function. The results show that an elevation of blood uric acid levels due to a functional decline of Abcg2 can not be explained by a uric acid excretion from the kidney, and that the blood uric acid levels increase due to a decrease of a uric acid excretion via Abcg2 from organs other than the kidney. Also, they found that, in patients having blood uric acid levels increased due to a functional decline of ABCG2, a urinary uric acid excretion clearance does not decrease but rather shows an increasing tendency.

Regarding the excretion pathway other than urine, there is a report showing that sweat glands excrete only a negligible degree of uric acid, and it is considered that uric acid is excreted mainly into feces other than in the pathway for the urinary excretion. It is considered that, with respect to the pathway excreted into feces, uric acid secreted from saliva, gastric juice, and bile is each about 5% or below of uric acid excreted per day from the body. Accordingly, it is difficult to explain the elevation of blood uric acid levels even if these pathways are blocked. From these facts, it is likely that the decrease of uric acid excretion in the small intestine contributes to the elevation of blood uric acid levels due to an ABCG2 deficiency. In fact, the results of transport experiments using the small gut suggested that Abcg2 is involved in uric acid excretion from the small gut.

Use of an upstream portion of the small intestine in the transport experiments using the gut tract is based on a report showing that the expression of ABCG2 in human is high in an upper portion of the small intestine. Actually, the results of experiments performed using a lower portion of the small intestine also showed a weak urate transport as compared with that of an upstream portion, and a tendency showing no difference between wild-type mice and Abcg2-deficient mice was recognized. This suggests that gut tract secretion of uric acid via Abcg2 corresponds to its expression distribution, and is conducted mainly in an upper portion of the small gut.

Involvement of ABCG2 in uric acid excretion from the small gut suggests that blood uric acid levels can be decreased by inducing or activating ABCG2 of the digestive tract. Thus, the suggestion contributes to the development of a new blood uric acid level-lowering drug capable of using in patients having a renal failure.

Also, some hyperuricemia patients classified as those having a uric acid overproduction type in the traditional classification have a possibility that the cause is a uric acid underexcretion from the digestive tract, and therefore, the present invention contributes to diagnosis and prehension of a precise disease type of hyperuricemia, to suitable, effective use of therapeutic drugs, and to the development of therapeutic drugs based on a disease state.

Currently, for gout treatment, symptomatic therapy using NSAIDs is conducted during an attack. In addition, allopurinol which suppresses uric acid production, benzbromarone, probenecid and the like which are inhibitory drugs of uric acid reabsorption is prophylactically used for the purpose of retaining blood uric acid levels at a lower level. However, drugs accelerating urinary excretion are accompanied with a risk of urinary calculus as a side effect. Inhibition of ABCG2 is not desirable for improvement of hyperuricemia and lowering of a onset risk of gout. Instead, drugs causing induction of ABCG2 expression and enhancement of ABCG2 function are more suitable. Alternatively, drugs which do not lower the ABCG2 function but cause lowering of expression of URAT1 and GLUT9 and inhibition of their functions are more suitable.

Also, a clinical classification of hyperuricemia and selection of therapeutic drugs can be practiced more suitably by typing of SNPs of ABCG2 or evaluation of a uric acid excretion (detailed evaluation of a uric acid excretion amount in excreta and simple evaluation of a uric acid excretion pattern in a spot urine, in the latter case, reliability can be more increased by correcting on the basis of physical constitutions such as body weight).

From the above facts, it is identified that a combination of Q126X variation and other function-declining variation in an ABCG2 gene is a main cause of primary gout. These findings suggest the importance of non-functional variants of ABCG2 such as Q126X, which substantially inhibit urate excretion and cause gout.

Accordingly, the present invention provides, as a high-capacity urate transporter, a transporter which is formed from a protein having ABCG2 and is capable of selectively and ATP-dependently excreting urate, and preferably a transporter having no function-declining SNP such as at least Q126X.

Also, a combination of a function-losing variation such as Q126X and a half function-losing variation (Q141K) plays an important role in elevation of serum uric acid levels and the onset of gout. Accordingly, when the subject has one function-losing variation such as Q126X, in a simple examination, it is also possible to evaluate that the subject has a factor of urate transport-related diseases and inflammation-related diseases such as gout.

The method for evaluating urate transport-related disease factor and inflammation-related disease factor according to the present invention is a method for evaluating whether or not the subject has a factor that is capable of inducing urate transport failure, or a state or disease attributable to that failure, the method including a step for detecting variations in genes that encode an ABCG2 protein using a sample containing human genes of the subject.

Genes encoding the ABCG2 protein include V12M, R113X, Q126X, Q141K, F208S, G268R, E334X, S441N, L447V, S486N, F506SfsX4, R575X, and C608X, and, when an SNP or a gene polymorphism having a relationship of linkage disequilibrium with the SNP is detected in the subject, it is concluded that the subject has the factor.

Also, when the subject has a functional change of ABCG2 including a functional failure thereof without being limited to SNPs producing the above amino acid variations, it can be concluded that the subject has a factor that is capable of inducing urate transport failure, or a state or disease attributable to that failure.

Examples of such a functional change of ABCG2 including a functional failure thereof include a functional change of ABCG2 by a gene variation other than the above amino acid variations, a functional change of ABCG2 based on a change of an expression amount and the like by a gene variation in exons and introns containing a promoter and an untranslated region (UTR) of ABCG2, a functional change of ABCG2 by a change of a regulating factor such as a transcription factor, a compound and the like, a functional change of ABCG2 by CNV (copy number variant), an epigenetic change including DNA methylation, a functional change of ABCG2 by an RNA including a micro RNA and a noncoding RNA, and a functional change of ABCG2 by a change of a stabilization mechanism of the ABCG2 protein.

Examples of urate transport-related diseases and inflammation-related diseases include hyperuricemia, gout, rheumatoid arthritis, osteoarthritis, infertility, cerebral stroke, an ischemic heart disease, arrhythmia (including atrial fibrillation), photosensitivity, a chronic kidney disease and the like.

For example, infertility and photosensitivity were found in a study of hyperuricemic pedigrees having a functional decline of ABCG2. Also, it was confirmed that atrial fibrillation is found in cases having a functional decline of ABCG2. These facts suggest that these diseases may relate to a functional decline of ABCG2.

Also, a higher serum uric acid level is apt to develop urate transport-related diseases and inflammation-related diseases. Accordingly, when the level is equal to or more than a given level such as, for example, 8.0 mg/dl, it can be concluded that it is highly possible the subject has a factor that is capable of inducing urate transport failure, or a state or disease attributable to that failure. The threshold level may be changed suitably, for example, to 7 or 9.

The ABCG2 gene includes cDNAs derived from human, homogeneous genes derived from human which hybridize with a DNA consisting of a complementary base sequence under a stringent condition and which encode a polypeptide having a urate transport capability, and homologues thereof in mammals.

Determination of gene polymorphisms can be performed, using human blood or tissues as a material, by a direct sequencing method, a BAC array CGH method, a FISH method, an RFLP method, a PCR-SSCP method, an allele-specific oligonucleotide hybridization method, a TaqMan PCR method, an invader method, an HRM method, a SmartAmp method, a Q-probe method (QP method), a MALDI-TOF/MS method, a molecular beacon method, an RCA method, a UCAN method, a nucleic acid hybridization method using a DNA chip or a DNA microarray and the like.

SNPs can be detected directly from a genomic DNA, for example, by a direct sequencing method and the like.

Also, a particular genome DNA region may be amplified using a clone, or a PCR method, an LCR method, an SDA method, an RCK method, a LAMP method, a NASBA method and the like, and subsequently, determination of a base sequence of a portion of an allele containing at least a polymorphic site, detection by a probe specifically hybridizing with a polymorphic site, and measurement of a molecular weight of a gene fragment containing a polymorphic site may be performed.

SNPs of an amplified product can be determined by determination of the base sequence, measurement of the molecular weight by a MALDI-TOF mass analysis and the like, analysis of the restriction enzyme fragment length, detection by SSCP, electrophoresis and the like.

For example, the TaqMan method is a method in which a hybridization of an allele-specific oligonucleotide with a template is carried out concomitantly with a PCR method, and SNPs are detected using a fluorescence energy transfer phenomenon. When an allele-specific probe labeled with a fluorescent dye and a quencher is hybridized with a target site and PCR is carried out using a primer designed to amplify a region including that site, the hybridized probe is cleaved by a 5' nuclease activity of Taq polymerase, concomitantly with the progress of an extension reaction from the primer. Separation of the fluorescent dye and the quencher yields a fluorescence, and amplification of the template by the PCR reaction exponentially enhances a fluorescence intensity. By labeling two allele-specific probes with different fluorescent dyes, it is also possible to distinguish between a homozygote and a heterozygote in one assay.

The invader method is a method using two oligonucleotide probes, and is based on an enzyme reaction which recognizes and cleaves a specific structure formed between these probes and a template DNA. A target base sequence is recognized by two different probes, i.e., an invader probe substantially complementary to a first site of the target base sequence, and an allele probe which, on its 3'-terminal side, is substantially complementary to a second site of the target base sequence and which, on its 5'-terminal side, contains a flap not complementary to the template and forming a single strand. When these probes hybridize with adjacent regions of the template, the 3'-terminus of the invader probe invades an SNP site, and the structure is cleaved by an enzyme to release the flap. By labeling the flap previously, it is possible to quantify the flap released. By preparing two sets of flap-FRET probes and labeling them by different fluorescent dyes, it is possible to distinguish between a homozygote and a heterozygote in one assay.

The MALDI-TOF mass analysis is a method in which a primer adjacent to an SNP site is prepared, a primer extension reaction of only one base is carried out using a PCR-amplified sample DNA as a template and using ddNTP, and the ddNTP added is identified by a mass analysis of extension reaction products. The method does not need any fluorescent label of the primer, and can treat a large number of samples in a short time.

The RCA method is a method in which a DNA-amplifying means (a DNA polymerase moves on the template and synthesizes a long complementary DNA using a circular single-stranded DNA as a template) is applied to SNP typing. Identification of an SNP is carried out by the presence or absence of amplification via the RCA method. Thus, a single-stranded probe, which can anneal with a genomic DNA and can become circular, is hybridized with a genomic DNA to carry out the chain reaction. In case the terminus of the probe is set to an SNP site to be identified, matching of the site leads to amplification via RCA because of linkage and circularization, but mismatching does not lead to RCA amplification because of no linkage and no circularization. The SNP can be determined by identification of these two amplification reactions.

The DNA chip method is a method in which hybridization with a PCR-amplified, fluorescence-labeled cDNA or CRNA is carried out using a DNA chip prepared by arranging oligonucleotide probes containing a polymorphic site on a microarray. The method can detect many SNPs rapidly.

Methods for determining polymorphisms in an amino acid sequence include, for example, a proteome analysis by a two-dimensional electrophoresis method or a microfluidics method, peptide mapping and an amino acid sequence analysis using a mass spectroscope, an amino acid sequence analysis by a protein sequencer, a method for detecting the interaction between a polypeptide and a ligand using a protein chip and the like.

For example, the two-dimensional electrophoresis method usually conducts isoelectric point electrophoresis for the first dimension and SDS-PAGE for the second dimension, and can separate several thousand proteins on one plate of gel. For the isoelectric point electrophoresis, an amphoteric carrier or an immobilized pH gradient gel strip is used. For the SDS-PAGE, a continuous buffer solution system using one buffer solution having a certain pH or a discontinuous buffer solution system using multiple buffer solutions having a different pH is used. It is also possible to use a low BIS concentration gel electrophoresis, a concentration gradient gel electrophoresis, tricine-SDS-PAGE and the like, depending on the type of proteins to be separated. The proteins separated can be detected using Coomassie Blue staining or silver staining or using a fluorescent reagent on the gel in a good sensitivity. It is also possible to use a western blotting method using an antibody against an ABCG2 polypeptide.

The MALDI-TOF/MS method which is one of mass analysis methods is a method in which a protein sample is mixed with a matrix absorbing a laser beam such as sinapic acid, the mixture is dried and then irradiated with a high-energy pulse laser beam, ionization of the protein sample is carried out by energy transfer from the matrix, and a molecular weight of the ion is analyzed on the basis of the difference in flight time of a molecular ion of the sample by an initial acceleration. In order to fragmentize a peptide in the inside of a mass spectrometer and to obtain an amino acid sequence, an amino acid composition or the like by mass analysis of a fragment, a tandem mass spectrometry in which multiple mass separation portions are linked is used, and an analyzer of a triple quadrupole type using an electrospray ionization method, of a hybrid type, or of an ion trap type and other analyzers are also used.

The protein chip method can carry out comprehensively and rapidly the interaction of a sample with proteins, peptides, antibodies, expressed proteins and the like arranged on a basal plate.

The evaluation kit according to the present invention is a kit for evaluating whether or not the subject has a factor that is capable of inducing urate transport failure, or a state or disease attributable to that failure, the method including means for detecting at least one SNP of V12M, R113X, Q126X, Q141K, F208S, G268R, E334X, S441N, L447V, S486N, F506SfsX4, R575X, and C608X in an ABCG2 gene, or a gene polymorphism having a relationship of linkage disequilibrium with the SNP, using a sample containing human genes of the subject.

Thus, the means may be provided as a primer pair for amplifying a polynucleotide containing a polymorphism of the ABCG2 gene or a DNA fragment containing a polymorphism, or a polynucleotide for detecting a polymorphism.

Examples of polynucleotides include both polyribonucleotides and polydeoxyribonucleotides. They may be unmodified RNAs or DNAs, modified RNAs or DNAs, and include, for example, DNAs, cDNAs, genomic DNAs, mRNAs, unprocessed RNAs, their fragments and the like.

Also, polypeptides are those in which two or more amino acids are linked by a peptide bond, and include relatively short chain peptides or oligopeptides, and also long chain peptides referred to as proteins. The polypeptides may contain amino acids other than 20 amino acids encoded genetically, and modified amino acids. The modification includes acetylation, acylation, ADP-ribosylation, amidation, biotinylation, a covalent bond with lipids and lipid derivatives, formation of a cross-linking bond, a disulfide bond, addition of a sugar chain, addition of a GPI anchor, phosphorylation, prenylation and the like in a main chain of peptide bonds, a side chain of amino acids, an amino-terminus, and a carboxyl-terminus.

The method for examining urate transport kinetics according to the present invention uses nonhuman animals having a deficiency of an ABCG2 gene, and includes a step for measuring their serum uric acid levels. Also, the nonhuman animals having a deficiency of an ABCG2 gene may be provided as means for examining the urate transport kinetics.

Nonhuman animals include, for example, mammals such as mouse, and also include tissues and cells constituting their body. Also, samples are those containing polynucleotides derived from organisms, and include body fluid, skin, hair root, mucosal membrane, internal organs, placenta, cord blood and the like collected from tissues and cells.

Similarly, nonhuman animals overexpressing a human ABCG2 gene or a nonhuman ABCG2 gene, nonhuman animals overexpressing a human ABCG2 gene or a nonhuman ABCG2 gene containing at least one variation of V12M, R113X, Q126X, Q141K, F208S, G268R, E334X, S441N, L447V, S486N, F506SfsX4, R575X, and C608X, nonhuman cell lines or human cell lines having a deficiency of an ABCG2 gene, nonhuman cell lines or human cell lines overexpressing a human ABCG2 gene or a nonhuman ABCG2 gene, nonhuman cell lines or human cell lines overexpressing a human ABCG2 gene or a nonhuman ABCG2 gene containing at least one variation of V12M, R113X, Q126X, Q141K, F208S, G268R, E334X, S441N, L447V, S486N, F506SfsX4, R575X, and C608X, or cell membrane vesicles prepared from these cell lines may be used.

The drug for urate transport-related diseases and inflammation-related diseases according to the present invention is a drug for reducing a factor that is capable of inducing urate transport failure, or a state or disease attributable to that failure, and contains a polynucleotide encoding an ABCG2 protein in the form capable of introducing it into cells or a polypeptide corresponding to an ABCG2 protein in the form capable of introducing it into cells. The former drug can stably improve the urate transport for a long period, and the latter drug can conveniently improve the urate transport by administration via injection and the like.

The form capable of introducing a polynucleotide into cells means a form allowing introduction of the polynucleotide into cells and expression of ABCG2 encoded so that an intracellular ABCG2 gene expresses the ABCG2. Similarly, the form capable of introducing a polypeptide into cells means a form allowing introduction of the polypeptide into cells and exertion of a function similar to that of the ABCG2 in cells.

ABCG2 polynucleotides can be obtained by a method of screening an existing cDNA library using an oligonucleotide probe prepared on the basis of a known nucleotide sequence, or a method such as RT-PCR using an oligonucleotide primer.

ABCG2 not having any SNP of V12M, R113X, Q126X, Q141K, F208S, G268R, E334X, S441N, L447V, S486N, F506SfsX4, R575X, and C608X, and ABCG2 not having at least an SNP of Q126X are preferred. To obtain a form capable of introducing the ABCG2 polynucleotide into cells, for example, a method using the polynucleotide as a bare DNA, or a method formulating the polynucleotide in a form of a recombinant virus vector is used. Virus vectors include those derived from genomes of viruses belonging to Baculoviridae, Parvoviridae, Picornoviridae, Herpesviridae, Poxyiridae, Adenoviridae, Picornaviridae and the like.

Also, a polynucleotide expression vector may be introduced into tissues or cells removed from a living body, and then, the tissues or cells may be returned to the living body. In such a case, a method can be used in which an expression vector integrating a polynucleotide is introduced into cells by transfection such as, for example, a microinjection method or an electroporation method.

The polynucleotide in a virus vector or an expression vector may be linked under a control of a promoter inducing systemic or tissue-specific expression. When a kidney-specific infection with a virus vector is carried out, it is possible to introduce a recombinant vector by inserting a catheter into an artery transdermally and then inserting the catheter into a kidney artery with checking the location of the catheter by X-rays.

An ABCG2 polypeptide can be prepared by a genetic engineering technique using the above ABCG2 polynucleotide. Thus, the ABCG2 polypeptide can be obtained in vitro by preparing an RNA by an in vitro transcription from a vector containing the polynucleotide, and carrying out an in vitro translation using it as a template. In case the polynucleotide is integrated into an expression vector, it is also possible to obtain the ABCG2 polypeptide as an expression product from prokaryotic cells such as *Escherichia coli* or *Bacillus subtilis*, from yeast, or from eukaryotic cells such as insect cells or mammal cells.

Also, the ABCG2 polypeptide can be synthesized according to a known chemical synthesis method.

The ABCG2 polypeptide may be provided as a peptide derivative. Such a derivative contains a modification for accelerating synthesis and purification, a modification for accelerating physical and chemical stabilization, an activation modification such as stabilization and instabilization or conditioning for in vivo metabolism, and the like.

Other modifications in peptide derivatives include acetylation, acylation, ADP-ribosylation, amidation, a covalent bond of flavin, a covalent bond of a heme moiety, a covalent bond of nucleotides or nucleotide derivatives, a covalent bond of lipids or lipid derivatives, a covalent bond of phosphatidylinositol, cross-linking, cyclization, a disulfide bond, demethylation, formation of a cross-linking covalent bond, cystine formation, pyroglutamate formation, formylation, gamma-carboxylation, glycosylation, GPI-anchor formation, hydroxylation, iodination, methylation, myristoylation, oxidation, proteolytic processing, phosphorylation, prenylation, racemization, a lipid bond, sulfation, selenoylation and the like. More specifically, the peptide derivatives can be prepared in the form of a functional group produced as a side chain on the peptide residues or as an N-terminal group or a C-terminal group, in the range not destroying any activity of an ABCG2 polypeptide and not giving any toxicity to a composition containing the polypeptide. Examples thereof include derivatives containing a polyethylene glycol side chain which extends retainment of a polypeptide in the body fluid, aliphatic esters of a carboxyl group, amides of a carboxyl group by a reaction with ammonia or an amine, N-acyl derivatives of a free amino group on an amino acid residue formed with an acyl moiety, O-acyl derivatives of a free hydroxyl group formed with an acyl moiety and the like.

Also, the ABCG2 polypeptide may be provided in the form of a pharmaceutically acceptable salt. Such a salt includes both a salt of a carboxyl group and an acid addition salt of an amino group on the polypeptide.

Salts of a carboxyl group include, for example, inorganic salts such as sodium, calcium, ammonium, iron, or zinc salt, as well as salts with an organic base formed using an amine such as triethanolamine, arginine, lysine, piperidine, or procaine. Acid addition salts include, for example, salts with a mineral acid such as hydrochloric acid or sulfuric acid, as well as salts with an organic acid such as acetic acid or oxalic acid.

In order to formulate such an ABCG2 polypeptide in the form capable of introducing it into cells, for example, use of a fused polypeptide in which a cell membrane-permeating peptide is linked to an N-terminal side of the polypeptide is mentioned. PTD of HIV-1 TAT or PTD of *drosophila* homeobox protein Antennapedia can be used as the cell membrane-permeating peptide. The fused polypeptide can be prepared by a genetic engineering technique, for example, using a fused polynucleotide prepared by linking an ABCG2 polynucleotide and a PTD polynucleotide. Such a fused polypeptide can be introduced by inserting a catheter into an artery transdermally and then inserting the catheter into a kidney artery while checking the location of the catheter by X-rays to introduce a recombinant vector. It is also possible to prepare a fused polypeptide linked with a cell membrane-permeating peptide by a method for linking a polypeptide and a PTD peptide through a cross-linking agent such as EDC or β-alanine.

Industrial Applicability

The present invention effectively evaluates whether or not the subject has a factor that is capable of inducing urate transport failure, or a state or disease attributable to that failure, and therefore contributes to prevention and early treatment of various urate transport-related diseases. Also, the present invention contributes to treatment of urate transport-related diseases without causing other undesirable effects even after the onset. Accordingly, the present invention is effective against inflammation-related diseases such as hyperuricemia, gout, rheumatoid arthritis, osteoarthritis, infertility, cerebral stroke, an ischemic heart disease, arrhythmia (including atrial fibrillation), photosensitivity, and chronic kidney disease, and also against hypertension, obesity, diabetes, a coronary artery disease, a cerebrovascular disease, a kidney disease and the like which are likely to develop as a result of complications, and therefore is industrially useful.

The invention claimed is:

1. A high capacity urate transporter formulation, comprising:
   a polypeptide having (i) an amino acid sequence consisting of SEQ ID NO:62; and, (ii) a cell membrane permeating peptide;
   wherein, the polypeptide is a cross-linked polypeptide having the cell membrane permeating peptide linked to SEQ ID NO:62 through a cross-linking agent.

2. The formulation of claim 1, wherein the amino acid sequence consisting of SEQ ID NO:62 is synthetic.

3. The formulation of claim 1, wherein the amino acid sequence consisting of SEQ ID NO:62 is recombinantly produced.

4. The formulation of claim 1, wherein the cell membrane permeating peptide is the protein transduction domain of the HIV TAT protein.

5. The formulation of claim 1, wherein the cell membrane permeating peptide is the protein transduction domain of the *Drosophila* homeobox Antennapedia protein.

6. The formulation of claim 1, wherein the cross-linking agent is β-alanine.

7. The formulation of claim 1, wherein the cross-linking agent is EDC.

8. The formulation of claim 1, wherein the cell membrane permeating peptide is the protein transduction domain of the HIV TAT protein and the cross-linking agent is β-alanine.

9. The formulation of claim 1, wherein the cell membrane permeating peptide is the protein transduction domain of the HIV TAT protein and the cross-linking agent is EDC.

10. The formulation of claim 1, wherein the cell membrane permeating peptide is the protein transduction domain of the *Drosophila* homeobox Antennapedia protein and the cross-linking agent is β-alanine.

11. The formulation of claim 1, wherein the cell membrane permeating peptide is the protein transduction domain of the *Drosophila* homeobox Antennapedia protein and the cross-linking agent is EDC.

* * * * *